(12) United States Patent
Curtis et al.

(10) Patent No.: US 6,172,077 B1
(45) Date of Patent: Jan. 9, 2001

(54) SPIRO-AZACYCLIC DERIVATIVES AND THEIR USE AS THERAPEUTIC AGENTS

(75) Inventors: Neil Roy Curtis, Puckeridge; Jason Matthew Elliott, Felsted; Gregory John Hollingworth, Brentwood; Philip Stephen Jackson, Basildon; Janusz Jozef Kulagowski, Sawbridgeworth; Eileen Mary Seward, Bishops Stortford; Christopher John Swain, Duxford; Brian John Williams, Great Dunmow, all of (GB)

(73) Assignee: Merck Sharp & Dohme Ltd., Hoddesdon (GB)

( * ) Notice: Under 35 U.S.C. 154(b), the term of this patent shall be extended for 0 days.

(21) Appl. No.: 09/403,636

(22) PCT Filed: Apr. 22, 1998

(86) PCT No.: PCT/GB98/01179

§ 371 Date: Oct. 22, 1999

§ 102(e) Date: Oct. 22, 1999

(87) PCT Pub. No.: WO98/49170

PCT Pub. Date: Nov. 5, 1998

(30) Foreign Application Priority Data

Apr. 25, 1997 (GB) .................................................. 9708484

(51) Int. Cl.[7] ...................... A61K 31/445; C07D 491/107
(52) U.S. Cl. .............................................. 514/278; 546/16
(58) Field of Search ................................ 514/278; 546/16

(56) References Cited

FOREIGN PATENT DOCUMENTS

| 0 627 221 | 12/1994 | (EP) . |
|---|---|---|
| WO 94/20500 | 9/1994 | (WO) . |
| WO 96/20197 | 7/1996 | (WO) . |
| WO 97/19084 | 5/1997 | (WO) . |
| WO 98/13369 | 4/1998 | (WO) . |

*Primary Examiner*—Charanjit S. Aulakh
(74) *Attorney, Agent, or Firm*—J. Eric Thies; David L. Rose

(57) ABSTRACT

The present invention is directed to substituted spiro-azacyclic derivatives of the formula (I):

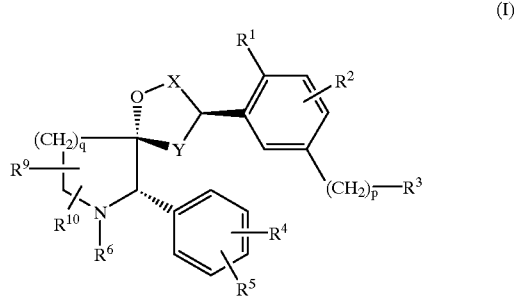

(wherein $R^1$, $R^2$, $R^3$, $R^4$, $R^5$, $R^6$, $R^9$, $R^{10}$, X, Y, p and q are defined herein) which are tachykinin antagonists and are useful, for example, in the treatment or prevention of pain, inflammation, migraine, emesis and postherpetic neuralgia.

15 Claims, No Drawings

SPIRO-AZACYCLIC DERIVATIVES AND THEIR USE AS THERAPEUTIC AGENTS

CROSS REFERENCE TO RELATED APPLICATIONS

This application claims priority under 35 U.S.C. 371 from PCT/GB98/01179, filed Apr. 22, 1998, which claims priority from Great Britain Application No. 9708484.2, filed Apr. 25, 1997.

This invention relates to a class of azacyclic compounds which are useful as tachykinin antagonists. More particularly, the compounds of the invention are spiro-substituted azacyclic derivatives.

International (PCT) patent specification no. WO 94/20500 (published Sep. 15, 1994) discloses spiroazacyclic derivatives as substance P antagonists. In particular, WO 94/20500 relates to spirocyclic piperdine derivatives containing a 1,8-diazaspiro[5.5]undecane core.

We have now found a further class of non-peptides which are potent antagonists of tachykinins, especially of substance P. In addition, the compounds of the present invention exhibit a high level of hepatic stability as measured by, for example, conventional liver microsome analysis.

The present invention provides compounds of the formula (I):

(I)

wherein

X represents $—CH_2—$, $—CH_2CH_2—$ or $—CH_2CH_2CH_2—$;

Y represents $—CH_2—$ or $—CH_2CH_2—$, with the proviso that the sum total of carbon atoms in X and Y is 2 or 3;

$R^1$ represents halogen, hydroxy, $C_{1-6}$alkyl, $C_{1-6}$alkoxy, $C_{1-6}$alkylthio, $C_{1-6}$alkoxyC$_{1-4}$alkyl, fluoroC$_{1-6}$alkyl, fluoroC$_{1-6}$alkoxy, fluoroC$_{1-6}$alkylthio, fluoroC$_{1-6}$alkoxyC$_{1-4}$alkyl, $C_{3-7}$cycloalkyl, $C_{3-7}$cycloalkylC$_{1-4}$alkyl, $C_{2-6}$alkenyloxy, cyano, phenoxy, benzyloxy, $NR^aR^b$, $SR^a$, $SOR^a$, $SO_2R^a$, or $OSO_2R^a$, where $R^a$ and $R^b$ each independently represent hydrogen, $C_{1-4}$alkyl or fluoroC$_{1-4}$alkyl;

$R^2$ represents hydrogen, halogen, $C_{1-6}$alkyl or $C_{1-6}$alkoxy;

or when $R^2$ is adjacent to $R^1$, they may be joined together such that there is formed a 5- or 6-membered saturated or unsaturated ring containing one or two oxygen atoms;

$R^3$ represents a 5- or 6-membered aromatic heterocyclic group containing 1, 2, 3 or 4 heteroatoms, selected from nitrogen, oxygen and sulphur, which group is optionally substituted by one or two groups selected from $C_{1-6}$alkyl, $C_{1-6}$alkoxy, $C_{3-7}$cycloalkyl, $C_{3-7}$cycloalkylC$_{1-4}$alkyl, trifluoromethyl, $OCF_3$, $NO_2$, CN, $SR^a$, $SOR^a$, $SO_2R^a$, $COR^a$, $CO_2R^a$, phenyl, $—(CH_2)_rNR^aR^b$, $—(CH_2)_rNR^aCOR^b$, $—(CH_2)_rCONR^aR^b$, or $CH_2C(O)R^a$, where $R^a$ and $R^b$ are each independently hydrogen or $C_{1-4}$alkyl and r is zero, 1 or 2;

$R^4$ represents hydrogen, halogen, $C_{1-6}$alkyl, $C_{1-6}$alkoxy, $CF_3$, $OCF_3$, $NO_2$, CN, $SR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ are as previously defined;

$R^5$ represents hydrogen, halogen, $C_{1-6}$alkyl, $C_{1-6}$alkoxy substituted by $C_{1-4}$alkoxy or $CF_3$ ;

$R^6$ represents hydrogen, $COR^a$, $CO_2R^a$, $COCONR^aR^b$, $COCO_2R^a$, $C_{1-6}$alkyl optionally substituted by a group selected from ($CO_2R^a$, $CONR^aR^b$, hydroxy, CN, $COR^a$, $NR^aR^b$, $C(NOH)NR^aR^b$, $CONHphenyl(C_{1-4}alkyl)$, $COCO_2R^a$, $CONHNR^aR^b$, $C(S)NR^aR^b$, $CONR^aC_{1-6}alkylR^{12}$, $CONR^{13}C_{2-6}alkenyl$, $CONR^{13}C_{2-6}alkynyl$, $COCONR^aR^b$, $CONR^aC(NR^b)NR^aR^b$, $CONR^a$heteroaryl, and phenyl optionally substituted by one, two or three substituents selected from $C_{1-6}$alkyl, $C_{1-6}$alkoxy, halogen and trifluoromethyl);

or $R^6$ represents a group of the formula $—CH_2C≡CCH_2NR^7R^8$ where $R^7$ and $R^8$ are as defined below;

or $R^6$ represents $C_{1-6}$alkyl, optionally substituted by oxo, substituted by a 5-membered or 6-membered heterocyclic ring containing 1, 2 or 3 nitrogen atoms optionally substituted by =O or =S and optionally substituted by a group of the formula $ZNR^7R^8$ where Z is $C_{1-6}$alkylene or $C_{3-6}$cycloalkyl;

$R^7$ is hydrogen or $C_{1-4}$alkyl, $C_{3-7}$cycloalkyl, $C_{3-7}$cycloalkylC$_{1-4}$alkyl, or $C_{2-4}$alkyl substituted by $C_{1-4}$alkoxy or hydroxyl;

$R^8$ is hydrogen or $C_{1-4}$alkyl, $C_{3-7}$cycloalkyl, $C_{3-7}$cycloalkylC$_{1-4}$alkyl, or $C_{2-4}$alkyl substituted by $C_{1-4}$alkoxy, hydroxyl or a 4, 5 or 6 membered heteroaliphatic ring containing one or two heteroatoms selected from N, O and S;

or $R^7$, $R^8$ and the nitrogen atom to which they are attached form a heteroaliphatic ring of 4 to 7 ring atoms, optionally substituted by one or two groups selected from hydroxy or $C_{1-4}$alkoxy optionally substituted by a $C_{1-4}$alkoxy or hydroxyl group, and optionally containing a double bond, which ring may optionally contain an oxygen or sulphur ring atom, a group S(O) or S(O)$_2$ or a second nitrogen atom which will be part of a NH or $NR^c$ moiety where $R^c$ is $C_{1-4}$alkyl optionally substituted by hydroxy or $C_{1-4}$alkoxy;

or $R^7$, $R^8$ and the nitrogen atom to which they are attached form a non-aromatic azabicyclic ring system of 6 to 12 ring atoms;

or Z, $R^7$ and the nitrogen atom to which they are attached form a heteroaliphatic ring to 4 to 7 ring atoms which may optionally contain an oxygen ring atom;

$R^9$ and $R^{10}$ each independently represent hydrogen, halogen, $C_{1-6}$alkyl, $CH_2OR^d$, oxo, $CO_2R^a$ or $CONR^aR^b$ where $R^a$ and $R^b$ are as previously defined and $R^d$ represents hydrogen, $C_{1-6}$alkyl or phenyl;

$R^{12}$ represents $OR^a$, $CONR^aR^b$ or heteroaryl;

$R^{13}$ represents H or $C_{1-6}$alkyl;

p is zero or 1; and q is 1 or 2;

and pharmaceutically acceptable salts thereof.

A preferred class of compound of formula (I) is that wherein $R^1$ is a $C_{1-4}$alkoxy, fluoroC$_{1-4}$alkoxy or $C_{3-5}$cycloalkoxy group.

A particularly preferred class of compound of formula (I) is that wherein $R^1$ is a methoxy, isopropoxy, trifluoromethoxy, 2,2,2-trifluoroethoxy, 2,2-difluoroethoxy, 2-fluoroethoxy, cyclopropoxy or cyclobutoxy, group, especially a methoxy or cyclopropoxy group.

Another preferred class of compound of formula (I) is that wherein $R^2$ is a hydrogen, fluorine or chlorine atom, especially a hydrogen atom.

A further preferred class of compound of formula (I) is that wherein $R^4$ is a hydrogen atom or a fluorine atom.

Another preferred class of compound of formula (I) is that in which $R^5$ is a hydrogen atom.

Also preferred is the class of compound of formula (I) in which $R^9$ and $R^{10}$ are both hydrogen atoms.

A further preferred class of compound of formula (I) is that wherein $R^6$ is a hydrogen atom.

Also preferred is the class of compound of formula (I) in which $R^6$ is a $C_{1-6}$alkyl group, in particular $CH_2$, $CH(CH_3)$ and $CH_2CH_2$ and especially $CH_2$, substituted by a 5-membered heterocyclic ring containing 2 or 3 nitrogen atoms as previously defined.

In particular, the 5-membered ring is a heterocyclic ring selected from:

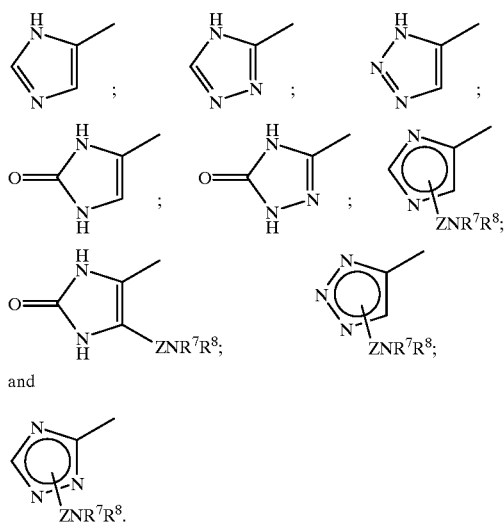

Particularly preferred heterocyclic rings are selected from:

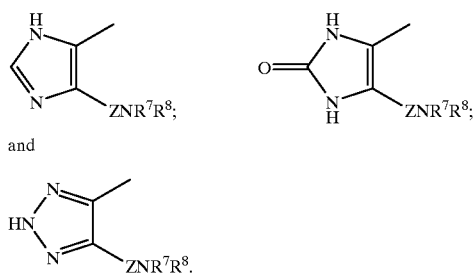

A particularly preferred heterocyclic ring is:

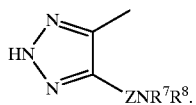

Where $R^1$ and $R^2$ are attached to adjacent carbon atoms and are joined together such that there is formed a 5- or 6-membered saturated or unsaturated ring containing one or two oxygen atoms, there is formed a fused ring moiety such as 2,3-dihydrobenzofuran, benzofuran, 3,4-dihydro-2H-1-benzopyran, 2H-1-benzopyran, 1,3-benzodioxole or 1,4-benzodioxan. Particularly preferred is 2,3-dihydrobenzofuran where the oxygen atom corresponds to the position of $R^1$.

Certain particularly apt compounds of the present invention include those wherein $R^3$ is a group selected from pyrrole, furan, thiene, pyridine, pyrazole, imidazole, oxazole, isoxazole, thiazole, isothiazole, pyrazine, pyrimidine, pyridazine, triazole, oxadiazole, thiadiazole, triazine, and tetrazole, each heteroaryl group being optionally substituted as previously defined.

Preferred compounds of the present invention are those wherein $R^3$ is a group selected from furan, pyridine, pyrazole, imidazole, oxazole, isoxazole, pyrazine, pyrimidine, thiazole, 1,2,3-triazole, 1,2,4-triazole 1,2,4-oxadiazole, 1,3,4-oxadiazole and tetrazole, each heteroaryl group being optionally substituted as previously defined.

Particularly preferred compounds of the present invention are those wherein $R^3$ is a group selected from furan, pyridine, pyrimidine, 1,2,3-triazole, 1,2,4-triazole and tetrazole, each heteroaryl group being optionally substituted as previously defined.

An especially preferred class of compound of formula (I) is that wherein $R^3$ is the group

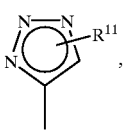

where $R^{11}$ is hydrogen, halogen, $C_{1-6}$alkyl, $C_{1-6}$alkoxy, $CF_3$, $OCF_3$, $NO_2$, $CN$, $SR^a$, $SOR^a$, $SO_2R^a$, $COR^a$, $CO_2R^a$, $(CH_2)_r$CONR$^a$R$^b$, $(CH_2)_r$NR$^a$R$^b$ or $(CH_2)_r$NR$^a$COR$^b$, where $R^a$ and $R^b$ are hydrogen or $C_{1-4}$alkyl, and r is zero, 1or 2.

Another especially preferred class of compound of formula (I) is that wherein $R^3$ is the group

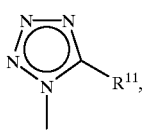

wherein $R^{11}$ is as previously defined.

$R^{11}$ is preferably hydrogen, $C_{1-4}$alkyl, especially methyl, $CF_3$, $(CH_2)_r$CONR$^a$R$^b$, SOR$^a$ or SO$_2$R$^a$ where $R^a$, $R^b$ and r are as previously defined. Most preferably, $R^{11}$ is hydrogen or $CF_3$.

Preferably X is —$CH_2$— or —$CH_2CH_2$—, especially —$CH_2$—.

Preferably Y is —$CH_2$—.

Preferably p is zero.

Preferably q is 2.

One favoured group of compounds of the present invention are of the formula (Ia) and pharmaceutically acceptable salts thereof:

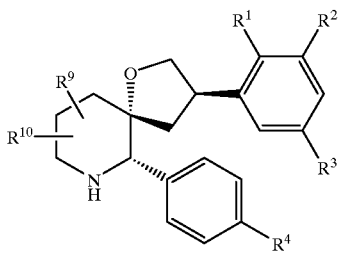

(Ia)

wherein $R^1$, $R^2$, $R^3$, $R^4$, $R^9$ and $R^{10}$ are as defined in relation to formula (I).

With respect to compounds of formula (I), Z (where present), may be a linear, branched or cyclic group. Favourably Z contains 1 to 4 carbon atoms and most favourably 1 or 2 carbon atoms. A particularly favourable group Z is $CH_2$.

With respect to compounds of formula (I), $R^7$ may aptly be a $C_{1-4}$alkyl group or a $C_{2-4}$alkyl group substituted by a hydroxyl or $C_{1-2}$alkoxy group, $R^8$ may aptly be a $C_{1-4}$alkyl group or a $C_{2-4}$alkyl group substituted by a hydroxyl or $C_{1-2}$alkoxy group, or $R^7$ and $R^8$ may be linked so that, together with the nitrogen atom to which they are attached, they form an azetidinyl, pyrrolidinyl, piperidyl, morpholino, thiomorpholino, piperazino or piperazino group substituted on the nitrogen atom by a $C_{1-4}$alkyl group or a $C_{2-4}$alkyl group substituted by a hydroxy or $C_{1-2}$alkoxy group.

Where the group $NR^7NR^8$ represents a heteroaliphatic ring of 4 to 7 ring atoms and said ring contains a double bond, a particularly preferred group is 3-pyrroline.

Where the group $NR^7NR^8$ represents a non-aromatic azabicyclic ring system, such a system may contain between 6 and 12, and preferably between 7 and 10, ring atoms. Suitable rings include
5-azabicyclo[2.1.1]hexyl, 5-azabicyclo[2.2.1]heptyl, 6-azabicyclo[3.2.1]octyl,
2-azabicyclo[2.2.2]octyl, 6-azabicyclo[3.2.2]nonyl, 6-azabicyclo[3.3.1]nonyl,
6-azabicyclo[3.3.2]decyl, 7-azabicyclo[4.3.1]decyl,
7-azabicyclo[4.4.1]undecyl and 8-azabicyclo[5.4.1]dodecyl, especially
5-azabicyclo[2.1.1]heptyl and 6-azabicyclo[3.2.1]octyl.

Where $R^8$ represents a $C_{2-4}$alkyl group substituted by a 5 or 6 membered heteroaliphatic ring containing one or two heteroatoms selected from N, O and S, suitable rings include pyrrolidino, piperidino, piperazino, morpholino, or thiomorpholino. Particularly preferred are nitrogen containing heteroaliphatic rings, especially pyrrolidino and morpholino rings.

In the group $ZNR^7R^8$, Z is preferably $CH_2$ or $CH_2CH_2$, and especially $CH_2$.

The group $NR^7R^8$ preferably represents amino, methylamino, dimethylamino, diethylamino, azetidinyl, pyrrolidino and morpholino.

In particular, $NR^7R^8$ is preferably dimethylamino, azetidinyl or pyrrolidino, especially dimethylamino.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the terms "fluoro$C_{1-6}$alkyl" and "fluoro$C_{1-6}$alkoxy" mean a $C_{1-6}$alkyl or $C_{1-6}$alkoxy group in which one or more (in particular, 1 to 3) hydrogen atoms have been replaced by fluorine atoms. Similarly, the terms "fluoro$C_{1-4}$alkyl" and "fluoro$C_{1-4}$alkoxy" means a $C_{1-4}$alkyl or $C_{1-4}$alkoxy group in which one or more (in particular 1 to 3) hydrogen atoms have been replaced by fluorine atoms. Particularly preferred are fluoro$C_{1-3}$alkyl and fluoro$C_{1-3}$alkoxy groups, for example, $CF_3$, $CH_2CH_2F$, $CH_2CHF_2$, $CH_2CF_3$, $OCF_3$, $OCH_2CH_2F$, $OCH_2CHF_2$ or $OCH_2CF_3$, and most especially $CF_3$, $OCF_3$ and $OCH_2CF_3$.

The cycloalkyl groups referred to herein may represent, for example, cyclopropyl, cyclobutyl, cyclopentyl or cyclohexyl. A suitable cycloalkylalkyl group may be, for example, cyclopropylmethyl.

As used herein, the terms "alkenyl" and "alkynyl" as a group or part of a group means that the group is straight or branched. Examples of suitable alkenyl groups include vinyl and allyl. A suitable alkynyl group is propargyl.

As used herein, the term "heteroaryl" as a group or part of a group means a 5- or 6-membered heteroaromatic ring containing 1 to 4 heteroatoms selected from N, O and S. Particular examples of such groups include pyrrolyl, furanly, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, and tetrazolyl.

When used herein the term "halogen" means fluorine, chlorine, bromine and iodine. The most apt halogens are fluorine and chlorine of which fluorine is preferred, unless otherwise state.

It will be appreciated that the preferred definitions of the various substituents recited above may be taken alone or in combination, and apply to the generic formula for compounds of the present invention as well as to the preferred class of compounds represented by formula (Ia).

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmaceutically inactive derivative of a biologically active substance (the "parent drug" or "parent molecule") that required transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 µm, particularly 0.1 and 0.5 µm, and have a pH in the range of 5.5 to 8.0.

Particularly preferred emulsion compositions are those prepared by mixing a compound of formula (I) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inset gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention futher provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, dental pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflux sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compounds of formula(I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents including those routinely used in cancer chemotherapy, and emesis induced by other pharmacological agents, for example, rolipram.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and*

*Vomiting: Recent Research and Clinical Advances,* Eds. J. Kucharczyk et al, CRC Press Inc., Boca Raton, Fla., U.S.A. (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralia et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-HT's antagonist, such as ondansetron, granisetron or tropisetron, or other anti-emetic medicaments, for example, a dopamine antagonist such as metoclopramide or $GABA_B$ receptor agonists such as baclofen. Additionally, a compound of formula (I) may be administered in combination with an anti-inflammatory cortcosteroid, such as dexamethasone, triamcinolone, triamcinolone acetonide, flunisolide, budesonide, or others such as those disclosed in U.S. Pat. Nos. 2,789,118, 2,990,401 3,048,581, 3,126,375, 3,929,768, 3,996,359, 3,928,326 and 3,749,712. Dexamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. pharmacol.,* (1993) 250, R5–R6, the compounds of the present invention are found to attenuate the retching and vomiting induced by cisplatin.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis, headache and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor agonist or tachykinin antagonist which acts at NK-2 receptors. The compound of formula (I) and the bronchodilator may be administered to a patient simultaneously, sequentially or in combination.

Likewise, a compound of the present invention may be employed with a keukotriene antagonists, such as a leukotriene $D_4$ antagonist such as a compound selected from those disclosed in European patent specification nos. 0 480 717 and 0 604 114 and in U.S. Pat. Nos. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator; and a pharmaceutically acceptable carrier.

It will be appreciated that for the treatment or prevention of migraine, a compound of the present invention may be used in conjunction with other anti-migraine agents, such as ergotamines or $5-HT_1$ agonists, especially sumatriptan, naratriptan, zolmatriptan or rizatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an antiinflammatory agent such as a bradykinin receptor antagonist.

It will be appreciated that for the treatment or prevention of pain or nociception, a compound of the present invention may be used in conjunction with other analgesics, such as acetaminophen (paracetamol), aspirin and other NSAIDs and, in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof. Preferred salts of these opioid analgesics include morphine sulphate, morphine hydrochloride, morphine tartrate, codeine phosphate, codeine sulphate, dihydrocodeine bitartrate, dacetylmorphine hydrochloride, hydrocodone bitartrate, hydromorphone hydrochloride, levorphanol tartrate, oxymorphone hydrochloride, alfentanil hydrochloride, buprenorphine hydrochloride, butorphanol tartrate, fentanyl citrate, meperidine hydrochloride, methadone hydrochloride, nalbuphine hydrochloride, propoxyphene hydrochloride, propoxyphene napsylate (2-naphthalenesulphonic acid (1:1) monohydrate), and pentazocine hydrochloride.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

It will be appreciated that for the treatment of depression or anxiety, a compound of the present invention may be used in conjunction with other anti-depressant or anti-anxiety agents.

Suitable classes of anti-depressant agent include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable atypical anti-depressants include: bupronion, lithium, nefazodone, trazodone and viloxazine, and pharmaceutically acceptable salts thereof.

Suitable classes of anti-anxiety agent include benzodiazepines and 5-HT$_{1A}$ agonists or antagonists, especially 5-HT$_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable 5-HT$_{1A}$ receptor agonists or antagonists include, in particular, the 5-HT$_{1A}$ receptor partial agonists buspirone, flesinoxan, gepirone and ipsaperone, and pharmaceutically acceptable salts thereof.

Therefore, in a further aspect of the present invention, there is provided a pharmaceutical composition comprising a compound of the present invention and an anti-depressant or anti-anxiety agent, together with at least one pharmaceutically acceptable carrier or excipient.

In a further or alternative aspect of the present invention, there is provided a product comprising a compound of the present invention and an anti-depressant or anti-anxiety agent as a combined preparation for simultaneous, separate or sequential use for the treatment or prevention of depression and/or anxiety.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 1 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to a general process (A.1), the compounds according to the invention in which X is —CH$_2$— and Y is —CH$_2$— or —CH$_2$CH$_2$—, may be prepared by the reduction of a compound of formula (IIA)

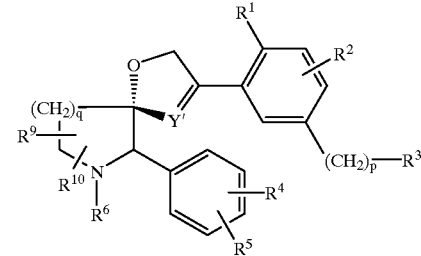

(IIA)

wherein $R^1$, $R^2$, $R^3$, $R^4$, $R^5$, $R^6$, $R^9$, $R^{10}$, p and q are as defined in relation to formula (I) and Y' is —CH= or —CH$_2$CH=

Suitable reducing conditions include: catalytic hydrogenation using a metal catalyst such as palladium or platinum or hydroxides or oxides thereof, preferably in a suitable solvent such as alcohol, e.g. methanol or ethanol, or an ester, e.g. ethyl acetate, or an organic acid e.g. acetic acid, or a mixture thereof.

Similarly, according to a general process (A.2), compounds of formula (I) may be prepared by the reduction of a compound of formula (IIB)

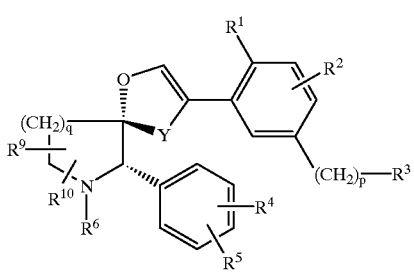
(IIB)

using the reaction conditions described in process (A.1), above.

According to another general process (B), compounds of formula (I) may be prepared by the interconversion of a corresponding compound of formula (I) in which $R^6$ is H, hereinafter referred to as formula (III)

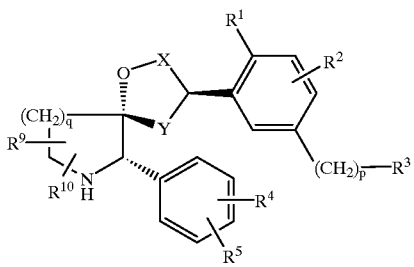
(III)

wherein X, Y, $R^1$, $R^2$, $R^3$, $R^4$, $R^5$, $R^9$, $R^{10}$, p and q are as defined in relation to formula (I) by reaction with a compound of formula (IV):

LG—$R^{6a}$ (IV)

where $R^{6a}$ is a group of the formula $R^6$ as defined in relation to formula (I) (other than H) or a precursor therefor and LG is a leaving group such as an alkyl- or arylsulphonyloxy group (e.g. mesylate or tosylate) or a halogen atom (e.g. bromine, chlorine or iodine); and, if $R^{6a}$ is a precursor group, converting it to a group $R^6$ (in which process any reactive group may be protected and thereafter deprotected if desired).

This reaction may be performed in conventional manner, for example in an organic solvent such as dimethylformamide in the presence of an acid accepter such as potassium carbonate.

Suitable alternative methods for introducing the group $R^6$ are described, for instance, in International Patent Specification No. WO 95/18124.

According to another general process (C), compounds of formula (I) wherein p is zero and $R^3$ is a tetrazol-1-yl group may be prepared by reaction of intermediates of formula (V)

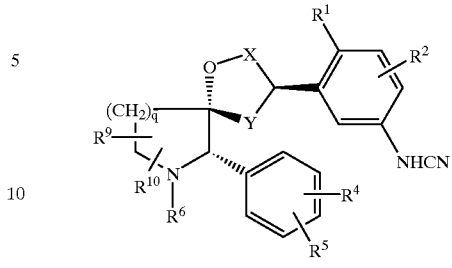
(V)

with ammonium chloride and sodium azide at elevated temperature, conveniently in a solvent such as dimethylformamide.

According to another general process (D), compounds of formula (I) may be prepared by a coupling reaction between a compound of formula (VIA) and (VIB)

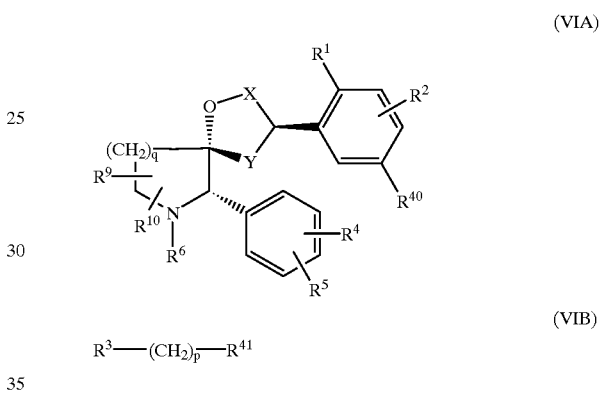
(VIA)

(VIB)
$R^3$—$(CH_2)_p$—$R^{41}$ wherein one of $R^{40}$ and $R^{41}$ is $B(OH)_2$ or $Sn(alkyl)_3$ or a derivative thereof, and the other is a leaving group such as a halogen atom e.g. bromine or iodine, or —$OSO_2CF_3$. Where one of $R^{40}$ and $R^{41}$ is $B(OH)_2$, the reaction is conveniently effected in the presence of a palladium (0) catalyst such as tetrakis(triphenylphosphine)palladium (0) in a suitable solvent such as an ether, for example, dimethoxyethane at an elevated temperature. Where one of $R^{40}$ and $R^{41}$ is $Sn(alkyl)_3$, the reaction is conveniently effected in the presence of palladium (II) catalyst such as bis(triphenylphosphine) palladium (II) chloride, in a suitable solvent such as an aromatic hydrocarbon, for example, toluene, at an elevated temperature.

According to another general process (E), compounds of formula (I) in which X is —$CH_2$—, may be prepared by the cyclisation of a compound of formula (VII)

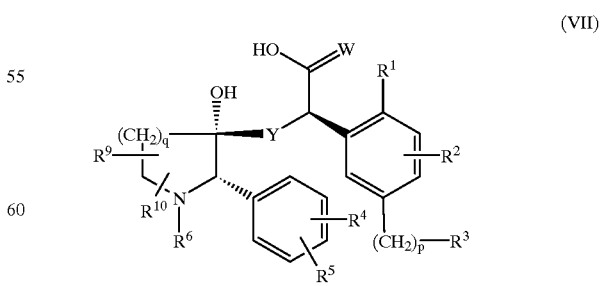
(VII)

wherein W is an oxygen atom or two hydrogen atoms, and using suitable dehydrating reagents, for example, methanesulphonyl chloride or benzenesulphonyl chloride in pyridine or triethylamine. The reaction is conveniently effected at a temperature between 0° C. and 100° C., preferably at between room temperature and 80° C., using a suitable organic solvent such as dichloromethane, where necessary.

Intermediates of formula (VII) are particularly preferred for controlling the stereochemistry of the 3-position in compounds of formula (I), especially where the 3(R) epimer is desired.

According to another general process (F), compounds of formula (I) in which $R^1$ is a cyclopropyloxy group, may be prepared from a compound of formula (VIII)

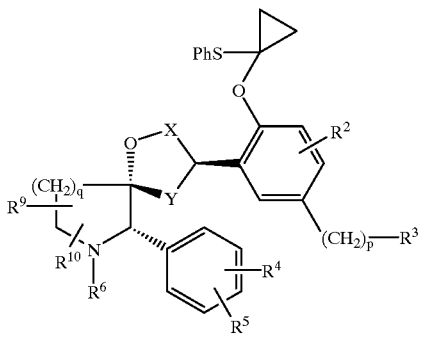

(VIII)

by reaction with lithium naphthalenide in tetrahydrofuran. The reaction is preferably effected at reduced temperature, for example at about −78° C.

According to another general process (G), compounds of formula (I) may be prepared from a compound of formula (IX)

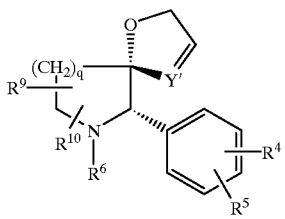

(IX)

wherein Y' is —CH= or —CH$_2$CH=, and a compound of formula (X),

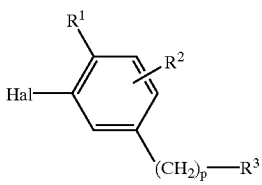

(X)

where Hal is chlorine, bromine or, preferably, iodine, by a reductive Heck reaction using a palladium catalyst such as palladium acetate with, for example, tri-o-tolylphosphine, dimethylformamide and tributylamine, or tetrabutylammonium chloride and dimethylformamide, and a reducing agent, preferably formic acid or a salt thereof, such as potassium formate.

Further details of suitable procedures will be found in the accompanying Examples.

Intermediates of formula (IIA) may be prepared by the dehydration of a compound of formula (XI)

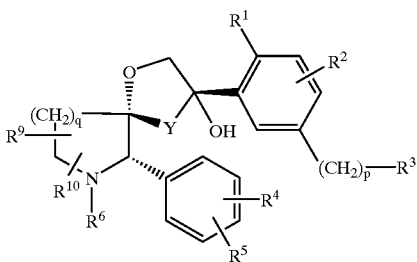

(XI)

Using an acid such as trifluoroacetic acid. The reaction is conveniently effected at a temperature between 0° C. and room temperature, using a suitable organic solvent such as dichloromethane.

Intermediates of formula (IIB) may be prepared using similar methodology.

Alternatively, intermediates of formula (IIA) are conveniently prepared by the reaction of a compound of formula (XII)

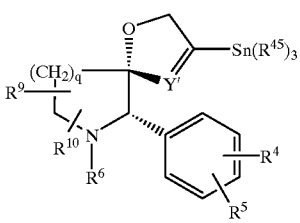

(XII)

wherein Y' is —CH= or —CH$_2$CH= and each $R^{45}$ is a $C_{1-4}$alkyl group, preferably methyl or n-butyl groups, with a compound of formula (X) wherein Hal is as previously defined, especially bromine.

The reaction is conveniently effected in the presence of lithium chloride and a transition metal catalyst such as triphenylphosphine palladium (0). Suitable solvents for the reaction include aromatic hydrocarbons, for example, toluene, the reaction being effected at a temperature between 80° C. and the reflux temperature of the solvent.

Intermediates of formula (III) may be prepared in a similar manner, preferably with an amino protecting group on the pyrrolidine/piperidine nitrogen in the compound of formula (XII). Suitable amino protecting groups include alkoxycarbonyl groups such as tert-butoxycarbonyl and trichloroethoxycarbonyl, aralkyloxycarbonyl groups such as benzyloxycarbonyl, or aralkyl groups such as benzyl. Removal of the protecting group is effected by conventional procedures thus, for example, tert-butoxycarbonyl groups may be removed under acidic conditions using, for example, trifluoroacetic acid; tert-butoxycarbonyl groups, together with benzyloxycarbonyl and benzyl groups, may also be removed by hydrogenolysis in the presence of a catalyst, for example, palladium; and trichloroethoxycarbonyl groups may be removed with zinc dust.

Compounds of formula (XII) may be prepared from a compound of formula (XIII)

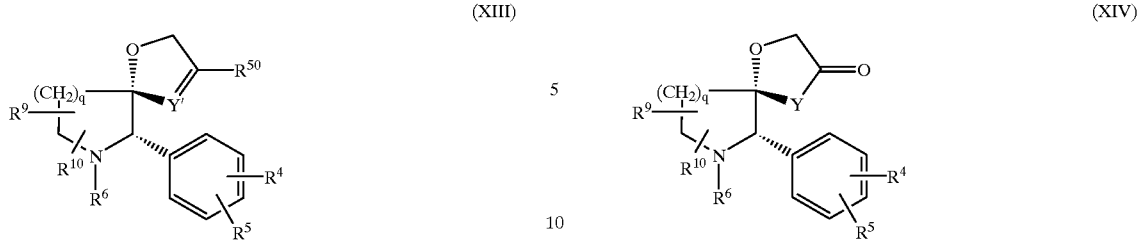

(XIII)

(XIV)

wherein $R^{50}$ is a triflate (—$OSO_2CF_3$) group or a bromine or iodine atom, by reaction with a compound of the formula $(R^{45})_3Sn$—$Sn(R^{45})_3$, for example, hexamethyl distannane. The reaction is conveniently effected in the presence of a base, for example, lithium carbonate, and a catalyst such as triphenylphosphine palladium(0). Suitable solvents for the reaction include ethers such as tetrahydrofuran, the reaction being effected at a temperature between room temperature and 100° C., for example, at about 60° C.

Compounds of formula (XIII) may be prepared from a compound of formula (XIV):

by enolisation of the ketone in the presence of a base, for example, sodium hexamethyldisilazide, followed by reaction with a reagent capable of introducing a suitable leaving group, for instance, where $R^{50}$ is —$OSO_2CF_3$, using 2-[N, N-bis(trifluoromethylsulphonyl)amino]-5-chloropyridine or triflic anhydride. The reaction is conveniently effected in a suitable solvent such as an ether, for example, tetrahydrofuran at a reduced temperature, for instance, -80° C.

Compounds of formula (XIV) may be prepared from a compound of formula (XV) by the following reaction sequences (Scheme A or Scheme B) or by methods analogous thereto (with the proviso that $R^9$ and $R^{10}$ are not oxo):

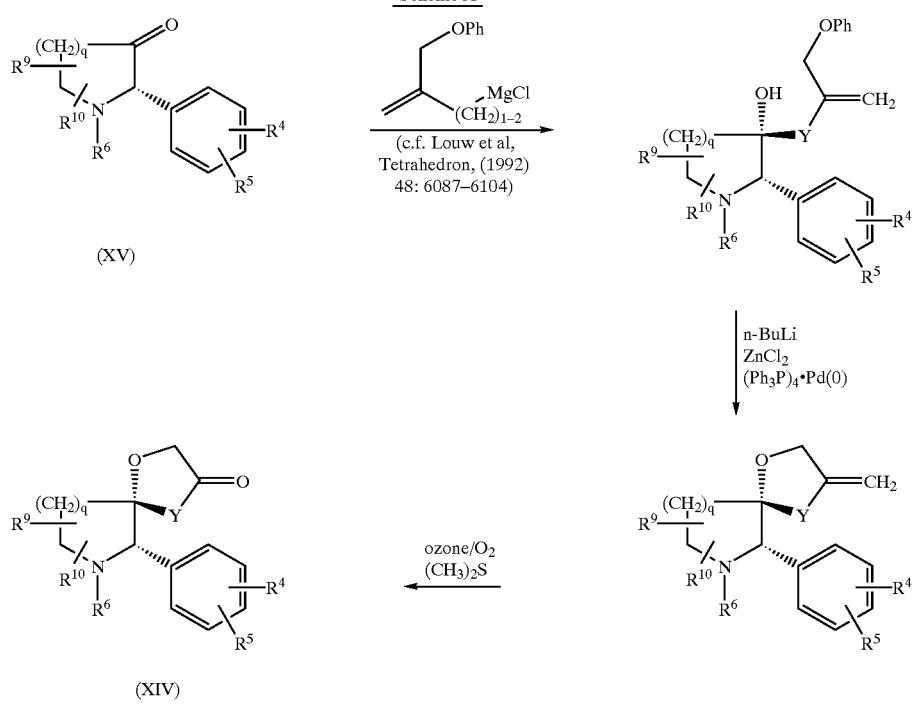

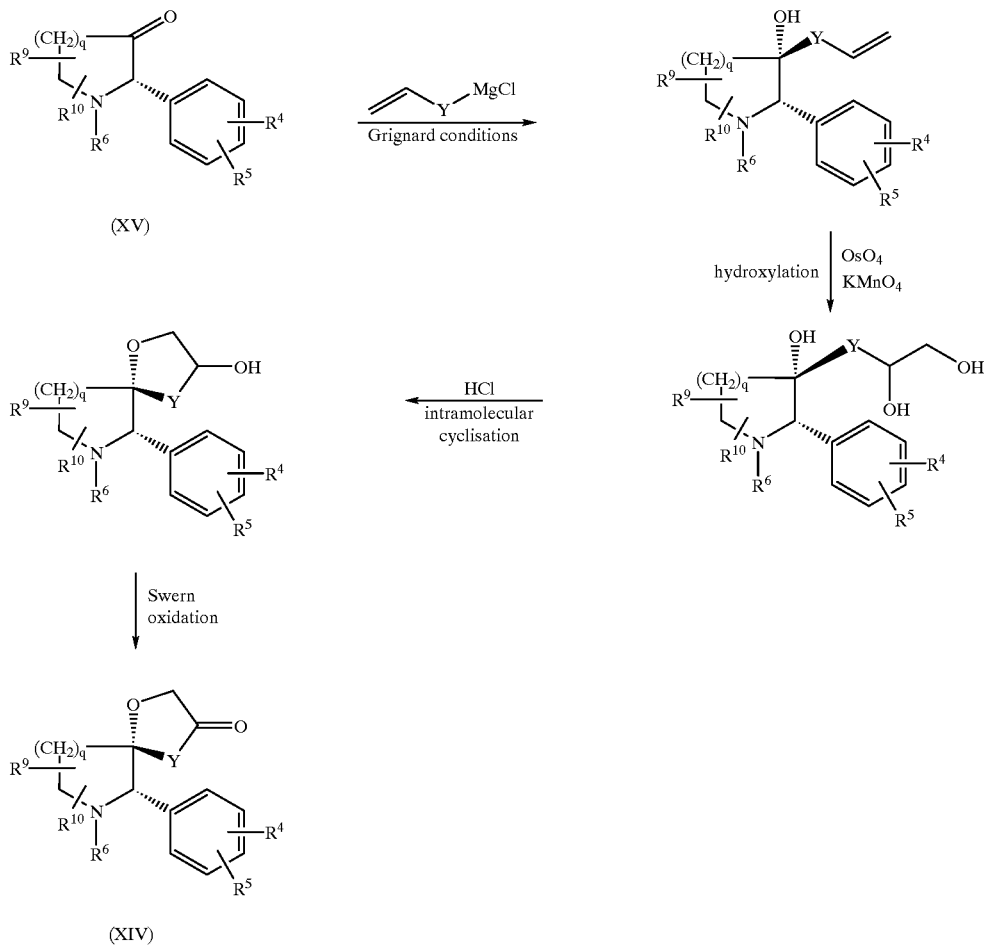
In an alternative method, compounds of formula (XII) where Y' is —CH= may be prepared by the following reaction sequence (Scheme C) or by methods analogous thereto:
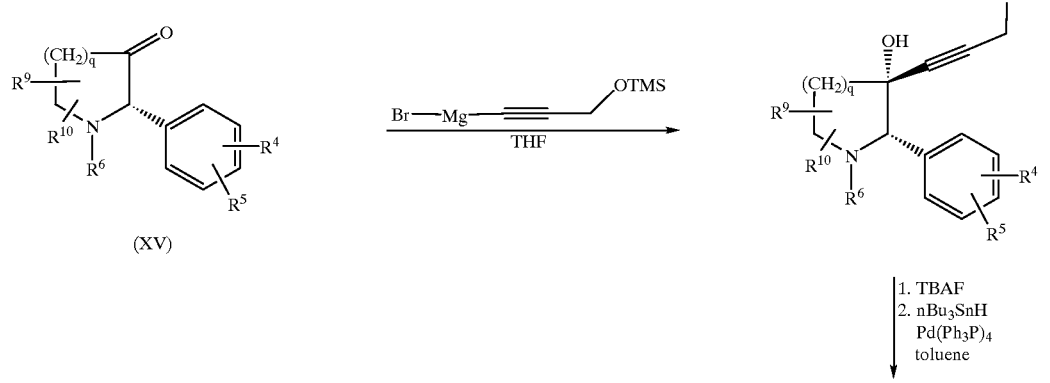

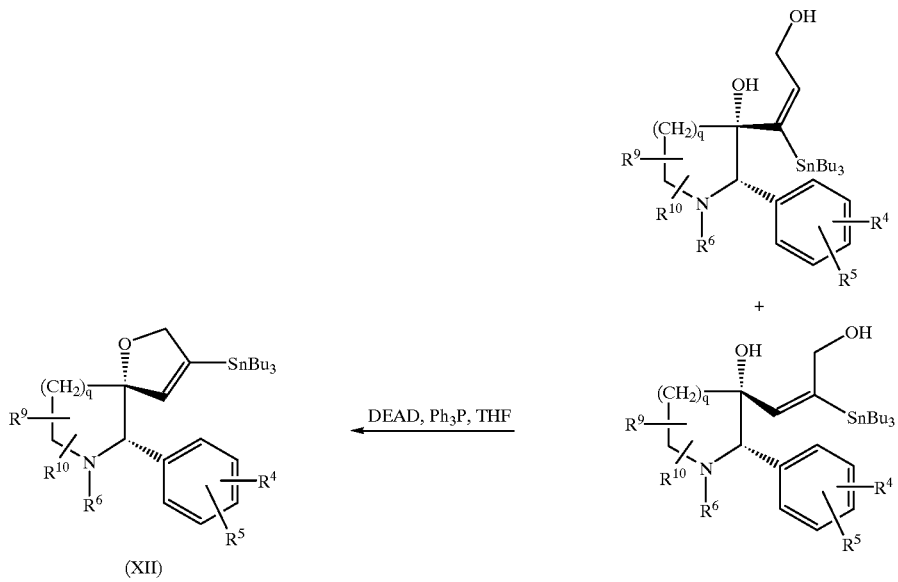

(XII)

In a preferred embodiment of the aforementioned processes, $R^6$ is replaced with an amino protecting group, in particular tert-butoxycarbonyl which is conveniently removed prior to reduction of the 7-aza-spiro[4.5]dec-3-ene structure (general process (A)).

In another preferred embodiment of the aforementioned processes, $R^6$ is a benzyl group. The reduction reaction described as process (A) above for the preparation of compounds of formula (I) may conveniently replace the benzyl group with a hydrogen atom. It will be appreciated from the discussion above that compounds of formula (I) wherein $R^6$ is a hydrogen atom are particularly preferred precursors to other compounds of formula (I).

Compounds of formula (X) in which p is zero and $R^3$ is an N-linked heterocyclic group may be prepared by conventional methodology, for example, from a compound of formula (XVI)

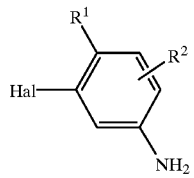

(XVI)

by reaction with a suitable anhydride of the formula $(R^{60}CO)_2O$, where $R^{60}$ is hydrogen or a desired substituent for the heterocycle, followed by reaction with triphenylphosphine in carbon tetrachloride, followed by the further step of (i) reaction with an azide such as sodium azide to effect the formation of a tetrazole ring; or (ii) reaction with hydrazine hydrate to effect the formation of a 1,2,4-trizole ring; or (iii) reaction with aminoacetaldehyde diethyl acetal to effect the formation of an imidazole ring.

Compounds of formula (XVI) may be prepared from the corresponding nitro compound by reduction using, for example, iron powder, or Raney nickel in a conventional manner.

The compounds of formula (XVI) or their nitro precursors are either known compounds or may be prepared using conventional methodology.

Compounds of formula (V) may be prepared by reacting a compound of formula (XVII)

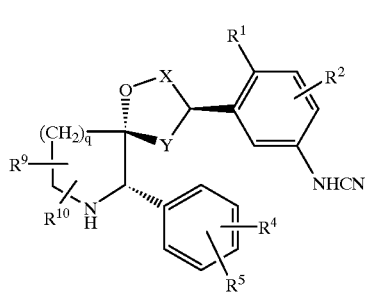

(XVII)

with any suitable reagent for completing the $R^6$ moiety as described, for example, in process (B).

Compounds of formula (XVII), and also compounds of formula (V), may be prepared by reaction of a compound of formula (XII) with a compound of formula (XVIII)

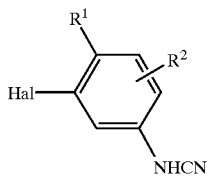

(XVIII)

according to the methods described above, followed, if necessary, by reduction according to the method of general process (A.1).

Intermediates of formula (XI) wherein Y is —$CH_2CH_2$— may be prepared by the reduction of a compound of formula (XIX)

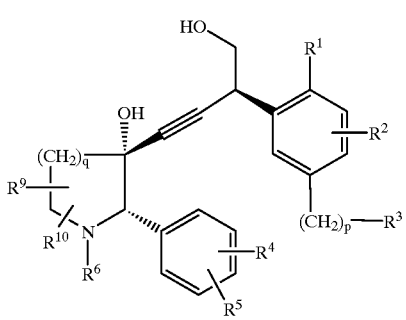

(XIX)

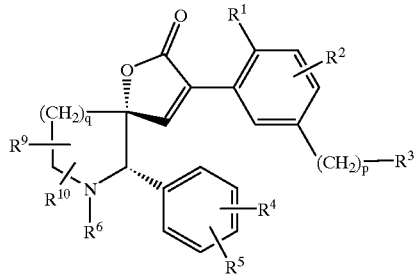

(XXII)

or a protected derivative thereof, using conventional methodology, for instance, by catalytic hydrogenation using a metal catalyst such as palladium or platinum or oxides thereof, preferably in a solvent such as an alcohol, e.g. ethanol, or an ester, e.g. ethyl acetate.

Compounds of formula (XIX) may be prepared by the reaction of a compound of formula (XV) with a compound of formula (XX)

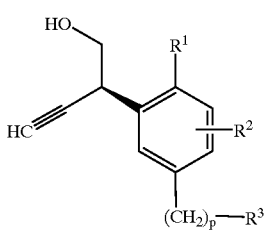

(XX)

or a protected derivative thereof, by lithiation using n-butyl lithium followed by quenching with, for example, sodium dihydrogen orthophosphate. The reaction is conveniently effected in a solvent such as an ether, e.g. tetrahydrofuran, at a reduced temperature, for example, at −78° C.

Compounds of formula (VII) where W is two hydrogen atoms may be prepared by reduction of a compound of formula (XXI)

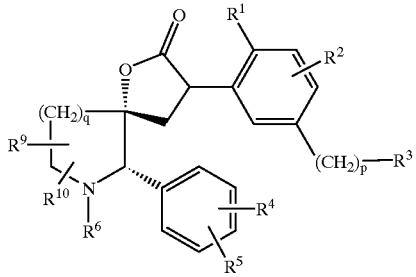

(XXI)

using, for example, a borohydride such as lithium borohydride, or lithium triethylborohydride in tetrahydrofuran, or a hydride such as lithium aluminium hydride or diisobutylaluminium hydride.

Compounds of formula (XXI) may be prepared by the reduction of a compound of formula (XXII)

using, for example, palladium acetate and potassium formate in a suitable solvent such as dimethylformamide at elevated temperature, for example at about 80° C.; or using catalytic hydrogenation with palladium or platinum hydroxide on carbon, preferably in a suitable solvent such as an alcohol, for example methanol, or an ester, for example ethyl acetate, or an organic acid, for example acetic acid, or a mixture thereof; or using sodium borohydride and nickel chloride.

Compounds of formula (XXII) may be prepared from a compound of formula (XXIII)

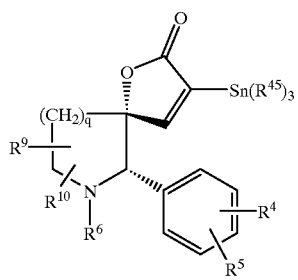

(XXIII)

according to the methods described herein.

Compounds of formula (XXIII) may be prepared, for example, from a compound of formula (XV) and ethyl propiolate and n-butyl lithium followed by treatment with trialkyltin hydride and palladium tetrakis triphenylphosphine in a manner analogous to that described in Scheme C.

In an alternative method, compounds of formula (VII) may be prepared by the reaction of a compound of formula (XV) with a Grignard reagent of formula (XXIV)

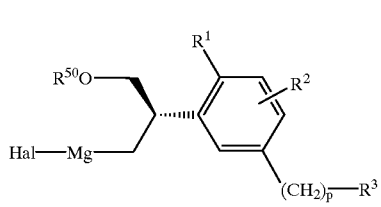

(XXIV)

wherein $R^{50}$ is a suitable hydroxy protecting group, preferably benzyl, and Hal is a halogen atom, preferably chlorine, followed by removal of the protecting group $R^{50}$. Utilisation of a chiral intermediate of formula (XXIV) is particularly suitable for controlling the sterochemistry of the 3-position in compounds of formula (I).

Compounds of formula (XXIV) may be prepared by conventional methods well known in the art or based upon the methods described in the Examples herein.

In a further alternative method, compounds of formula (VII) may be prepared by the reduction of a compound of formula (XXV)

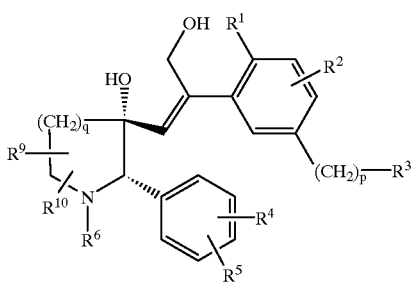
(XXV)

using, for example, catalystic hydrogenation in the presence of a metal catalyst such as palladium or platinum or hydroxides or oxides thereof, preferably in a suitable solvent such as an alcohol, e.g. methanol, an ester, e.g. ethyl acetate, or an organic acid, e.g. acetic acid, or a mixture thereof.

Compounds of formula (XXV) may be prepared from a compound of formula (XXVI)

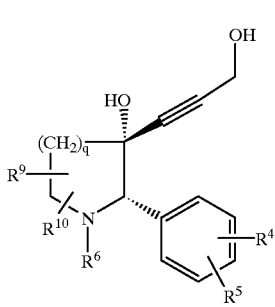
(XXVI)

by reaction with a compound of formula (X) using reductive Heck conditions as described in general process (G), above.

Compounds of formula (XXVI) may be prepared from compounds of formula (XV) and, for example, a Grignard reagent prepared from O-trimethylsilylpropargyl alcohol using conventional methodology, followed by removal of the hydroxy protecting group.

According to another method, compounds of formula (VII) may be prepared form a compound of formula (XXVII)

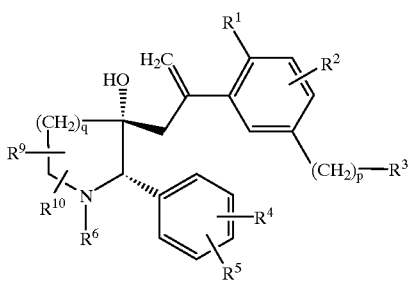
(XXVII)

by reaction with borane in tetrahydrofuran, followed by an oxidative work-up using, for example, hydrogen peroxide and sodium hydroxide.

Compounds of formula (XXVII) may be prepared from a compound of formula (XV) and, for example, a Grignard reagent prepared from a 2-aryl-3-bromo-1-propene using conventional methodology.

Compounds of formula (XI) may be prepared by the reaction of a compound of formula (XIV) with Grignard reagent prepared from a compound of formula (X), preferably using magnesium and a bromide of formula (X). The coupling reaction is conveniently effected at reduced temperature, for example at about 0° C., using a suitable solvent such as an ether, for example, diethyl ether.

Compounds of formula (VIII) may be prepared from a compound of formula (I) in which $R^1$ is a hydroxy group by reaction with (1-iodo-cycloprop-I-yl)phenylsulfide.

Compounds of formula (IX) may be prepared, for example, by the conversion of a stannane of formula (XII) to the corresponding iodide by treatment with iodine at reduced temperature, for example, at about −78° C., in a suitable solvent such as dichloromethane. The iodine may then be displaced to give the compound of formula (IX) by treatment with, for example, α,α'-azo-isobutyronitrile and tributyltin hydride in a suitable solvent, for example, toluene, at an elevated temperature, for example, at about 100° C.

Alternatively, compounds of formula (IX) may be prepared by the cyclisation of a compound of formula (XXVIII)

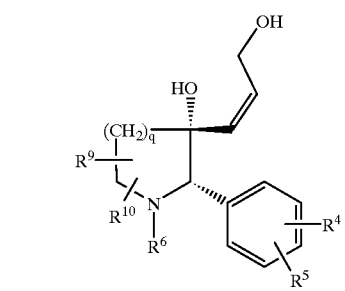
(XXVIII)

using the dehydrating conditions described above for general process (E) or using triphenylphosphine and diethylazodicarboxylate in a suitable solvent such as tetrahydrofuran.

Compounds of formula (XXVIII) may be prepared by the partial reduction of an acetylene compound of formula (XXVI). The reaction is conveniently effected by catalytic hydrogenation using a metal catalyst such as palladium on calcium carbonate in the presence of a lead poison (e.g. Lindlar catalyst). Other suitable methods will be readily apparent to a person of ordinary skill in the art.

Compounds of formula (XV) may be prepared by methods described in European Patent Specification No. 0 577 394-A, or by analogous methods.

Compounds of formula (XX) are known compounds (see *Chemische Berichte*, (1988) 121, 1315–1320) or may be prepared by methods analogous to those described therein.

Compounds of formula (VIB) and (XVIII) are known compounds or may be prepared by conventional methods or using techniques analogous to those taught herein.

It will be appreciated that compounds of the formula (I) wherein $R^6$ contains an =O or =S substituent can exist in tautomeric forms. All such tautomeric forms and mixtures thereof are included within this invention. Most aptly the =O or =S substituent in $R^6$ is the =O substituent.

Where they are not commercially available, the intermediates of formula (IV) above may be prepared by the procedures described in the accompanying Examples or by alternative procedures which will be readily apparent to one skilled in the art.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active and $IC_{50}$ at the $NK_1$ receptor of less than 100 nM on said test method.

For the avoidance of doubt, the nomenclature adhered to throughout this specification follows the general principle illustrated below:

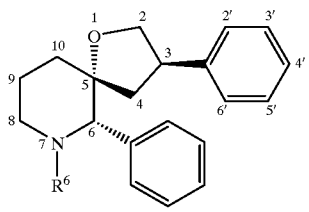

The following non-limiting Descriptions and Examples serve to illustrate the preparation of compounds of the present invention:

DESCRIPTION 1

(2S)-1-tert-Butoxycarbonyl-2-phenylpiperdin-3-one

Dimethyl sulfoxide (20.80 ml, 22.90 g, 29.3 mmol) in dichloromethane (75 ml) was added dropwise to a cooled (−70° C.) solution of oxalyl chloride (13.95 ml, 20.30 g, 160 mmol) in dichloromethane (350 ml). The mixture was stirred at −70° C. for 15 minutes, then (2S,3S)-1-tert-butoxycarbonyl-3-hydroxy-2-phenylpiperidine (prepared by the method described in European Patent Specification number 0 528 495-A; 36.91 g, 133 mmol) in dichloromethane (150 ml) was added dropwise. The mixture was stirred at −70° C. for 20 minutes, then allowed to warm to −30° C. The mixture was cooled to −50° C. and triethylamine (55.95 ml, 40.45 g, 400 mmol) was added slowly. The mixture was allowed to warm to 0° C. and diluted with ice-cooled dichloromethane (250 ml). The mixture was washed with ice cold aqueous citric acid solution (5%, 2×300 ml) and water (300 ml), dried (MgSO$_4$), and the solvent was evaporated under reduced pressure to give the title compound as a yellow oil (42.3 g), which was used immediately without further purification. $^1$H NMR (250 MHz, CDCl$_3$) δ 7.5–7.3 (5H, m), 5.8 (1H, br s), 4.2 (1H, br s), 3.4 (1H, m), 2.6 (2H, m), 2.0 (2H, m), and 1.54 (9H, s).

DESCRIPTION 2

(2S,3R)-1-tert-Butoxycarbonyl-3-(3-hydroxypropyn-1-yl)-2-phenylpiperidin-3-ol

O-Trimethylsilylpropargyl alcohol (24.51 ml, 20.47 g, 160 ml) was added slowly to a cooled (−10° C.) solution of ethylmagnesium bromide. (1M in tetrahydrofuran, 160 ml, 160 mmol). The mixture was stirred at 0° C. for 20 minutes, then at room temperature for 2 hours. The mixture was cooled to −10° C. and a solution of (2S)-1-tert-butoxycarbonyl-2-phenylpiperidin-3-one (Description 1; 42.3 g) in tetrahydrofuran (200 ml) was added dropwise over 30 minutes (Internal temperature below −5° C.). The mixture was stirred at room temperature for 14 hours, poured into water (300 ml) and saturated aqueous ammonium chloride (300 ml) and extracted with ethyl acetate (2×300 ml). The combined organic fractions were washed with brine (300 ml), dried (MgSO$_4$) and the solvent was evaporated under reduced pressure. The residue was dissolved in ethyl acetate (500 ml) and a solution of tetrabutylammonium fluoride (1M in tetrahydrofuran, 160 ml, 160 mmol) was added dropwise. The mixture was stirred at room temperature for 30 minutes, water (300 ml) was added, and the layers were separated. The aqueous layer was extracted with ethyl acetate (2×300 ml) and the combined organic fractions were washed with water (300 ml) and brine (300 ml), dried (MgSO$_4$) and the solvent was evaporated under reduced pressure to give the crude title compound as an orange oil (45 g). The crude material was purified by flash column chromatography on silica gel, eluting with hexane/ethyl acetate (90:10 increasing to 25:75) to give the title compound as an amber oil (32.2 g). $^1$H NMR (CDCl$_3$) δ 753–755 (2H, m), 7.19–7.35 (3H, m), 5.56 (1H, s), 4.27 (2H, s), 3.99–4.03 (1H, m), 3.25 (1H, br s), 2.77–2.81 (1H, m), 2.77 (1H, br s), 2.12–2.20 (1H, m), 1.91–1.99 (2H, m), 1.77–1.83 (1H, m), and 1.39 (9H, s).

DESCRIPTION 3

(5R,6S)-3-Tributylstannyl-6-phenyl-1-oxa-7-(tert-butoxycarbonyl)aza-spiro[4.5]dec-3-ene Crude (2S,3R)-1-tert-butoxycarbonyl-3-(3-hydroxypropyn-1-yl)-2-phenylpiperidin-3-ol (Description 2; 45 g) was dissolved in toluene (750 ml) and degassed with nitrogen. Tetrakis(triphenylphosphine)palladium (0) (2.30 g, 2.0 mmol) in toluene (600 ml) was added and the mixture was degassed. Tributyltin hydride (35.78 ml, 38.71 g, 133 mmol) was added dropwise over 15 minutes, with stirring and cooling (Internal temperature below 25° C.). The mixture was stirred at room temperature for 1 hour, then the solvent was evaporated under reduced pressure. The residue was dissolved in tetrahydrofuran (600 ml) and triphenylphosphine (34.88 g, 133 mmol) was added. A solution of diethyl azodicarboxylate (20.94 ml, 23.16 g, 133 mmol) in tetrahydrofuran (150 ml) was added dropwise with stirring and cooling and the mixture was stirred at room temperature for 1 hour. The solvent was evaporated under reduced pressure, acetonitrile (600 ml) was added and the mixture was extracted with hexane (8×150 ml). The hexane fractions were combined and the solvent was evaporated under reduced pressure. The residue was purified by flash column chromatography on silica gel, eluting with dichloromethane/ethyl acetate (100:0 increasing to 99:1) to give the title compound as a yellow oil (53.64 g, 67% from (2S,3S)-1-tert-butoxycarbonyl-3-hydroxy-2-phenylpiperidine). $^1$H NMR (CDCl$_3$) δ 7.38–7.40 (2H, m), 7.15–7.25 (3H, m), 5.96 (1H, t, J 2.3 Hz), 4.93 (1H, s), 4.63 (1H, dd, J 2.23, 12.9 Hz), 4.22 (1H, dd, J 2.23, 12.9 Hz), 4.09–4.14 (1H, m), 3.09–3.17 (1H, m), 1.95–1.99 (1H, m), 1.83–1.86 (1H, m), 1.72–1.76 (2H, m), 1.40–1.51 (6H, m), 1.38 (9H, s), 1.25–1.32 (6H, m), and 0.86–0.99 (15H, m).

DESCRIPTION 4

Z-(2S,3R)-1-tert-Butoxycarbonyl-3-(3-hydroxyprop-1-en-1-yl)-2-phenylpiperidin-3-ol Palladium on calcium carbonate, poisoned with lead (Lindlar catalyst, 2 g) was added to a solution of (2S,3R)-

1-tert-butoxycarbonyl-3-(3-hydroxypropyn-1yl)-2-phenylpiperidin-3-ol (Description 2; 32 g, 96.6 mmol) in ethyl acetate (300 ml) and the mixture was stirred under hydrogen (1 atmosphere) for 4 hours. The mixture was filtered and the solvent was evaporated under reduced pressure to give the title compound as an oil (32 g, 100%). $^1$H NMR (360 MHz, CDCl$_3$) δ 7.42 (2H, d, J 7.6 Hz), 7.35–7.25 (3H, m), 5.83 (1H, d, J 12.3 Hz), 5.68 (1H, dt, J 12.3, 6.0 Hz), 5.06 (1H, s), 4.27 (1H, m), 4.12 (2H, m), 3.32 (1H, m), 3.13 (1H, s), 2.28 (1H, t, J 5.9 Hz), 2.02 (1H, m), 1.92–1.78 (3H, m), and 1.32 (9H, s). m/z (ES$^+$) 334 (M+1).

DESCRIPTION 5

(5R,6S)-6-Phenyl-1-oxa-7-(tert-butoxycarbonyl)aza-spiro[4.5]dec-3-ene

Diethylazodicarboxylate (18.2 ml; 115 mmol) in THF (100 ml) was added dropwise to a solution of Z-(2S,3R)-1-tert-butoxycarbonyl-3-(3-hydroxyprop-1-en-1-yl)-2-phenylpiperidin-3-ol (Description 4; 32 g, 96 mmol) and triphenylphosphine (30.2 g, 115 mmol) in THF (700 ml). The mixture was stirred at 0° C. for 30 minutes then at room temperature for 1.5 hours. The solvent was evaporated under reduced pressure and the residue was purified by flash column chromatography on silica gel, eluting with hexane/ethyl acetate (95:5 increasing to 80:20) to give the title compound as a colorless solid (23.4 g, 77%). $^1$H NMR (CDCl$_3$) δ 7.45 (2H, d, J 7.4 Hz), 7.27 (2H, t, J 7.4 Hz), 7.20 (1H, t, J 7.4 Hz), 6.03 (1H, dt, J 6.1, 2.0 Hz), 5.68 (1H, dt, J 6.1, 2.0 Hz), 5.06 (1H, s), 4.61 (1H, dt, J 13.1, 2.0 Hz), 4.32 (1H, dt, J 13.1, 2.0 Hz), 4.08 (1H, m), 3.05 (1H, m), 2.05 (1H, m), 1.75 (3H, m), and 1.37 (9H, s). m/z (ES$^+$) 316 (M+I).

DESCRIPTION 6

2-Bromo-4-nitrophenol to a solution of 4-nitrophenol (75 g, 0.54 mol) in glacial acetic acid (700 ml) was added bromine (40 ml). The solution was stirred at room temperature under an atmosphere of nitrogen for 24 hours. The solvent was evaporated under reduced pressure and the residue was recrystallized from dichloromethane to give the title compound. $^1$H NMR (250 MHz, CDCl$_3$) δ 8.45 (1H, d, J 2.7 Hz), 8.16 (1H, dd, J 9.0 Hz and 2.6 Hz), 7.13 (1H, d, J 9.1 Hz), and 6.18 (1H, s).

DESCRIPTION 7

2-Benzyloxy-5-nitro-1-bromobenzene

A mixture of 2-bromo-4-nitrophenol (Description 6; 14 g, 68.6 mmol), benzyl bromide (14.1 g, 82.4 mmol) and potassium carbonate (47.3 g, 0.343 mol) in dimethylformamide (100 ml) was heated at 60° C. for 3 hours. The mixture was cooled to room temperature and poured into a mixture of ethyl acetate and water. The organic phase was washed with water (3 times) and saturated brine, dried (MgSO$_4$) and the solvent was evaporated under reduced pressure. The residue was recrystallized from methanol to give the title compound (19 g). H NMR (250 MHz, CDCl$_3$) δ 8.48 (1H, d, J 2.8 Hz), 8.18 (1H, dd, J 9.08 Hz, 2.8 Hz), 7.46–7.3 (5H, m), 7.0 (1H, d, J 9.2 Hz), and 5.27 (2H, s).

DESCRIPTION 8

5-Amino-2-benzyloxy-1-bromobenzene Hydrochloride

To a suspension of 2-benzyloxy-5-nitro1-bromobenzene (Description 7; 19 g, 61.7 mmol) in acetic acid (93 ml) and water (370 ml) was added iron powder (27.5 g, 0.49 mol). The mixture was heated to 80° C. for 2 hours, then filtered, washing the residue with ethyl acetate and water. The organic phase of the filtrate was washed with aqueous K$_2$CO$_3$, dried (MgSO$_4$) and the solvent was evaporated under reduced pressure. The residue was dissolved in methanol (50 ml) and methanolic hydrogen chloride (1M, 75 ml) was added. A crystalline solid was formed on standing which was collected and dried in vacuo to give the title compound (19.2 g). $^1$H NMR (250 MHz, DMSO-d$_6$) δ 7.56 (1H, d, J 1.3 Hz), 7.5–7.3 (7H, m), and 5.2 (2H, s).

DESCRIPTION 9

5-Trifluoroacetamido-2-benzyloxy-1-bromobenzene

5-Amino-2-benzyloxy-1-bromobenzene hydrochloride (Description 8; 19 g, 60.4 mmol) was suspended in dichloromethane (250 ml) and triethylamine (19 ml, 136.3 mmol) was slowly added. The solution was cooled (0° C.) and a solution of trifluoroacetic anhydride (10.7 ml, 75.8 mmol) in dichloromethane (20 ml) was slowly added. The solution was stirred for 16 hours and water was added. The organic phase was washed with saturated brine, dried (MgSO$_4$) and the solvent was evaporated under reduced pressure. The residue was purified by chromatography on silica gel, eluting with hexane/ethyl acetate, to give the title compound as a crystalline solid (21.6 g). $^1$H NMR (360 MHz, CDCl$_3$) δ 7.79 (1H, d, J 2.6 Hz), 7.76 (1H, br s), 7.5–7.31 (6H, m), 6.9 (1H, d, J 8.9 Hz), and 5.16 (2H, s).

DESCRIPTION 10

5-(1-Chloro-2,2,2-trifluoroacetimidato)-2-benzyloxy-1-bromobenzene

To a suspension of 5-trifluoroacetamido-2-benzyloxy-1-bromobenzene (Description 9; 21.6 g, 57.8 mmol) in carbon tetrachloride (255 ml) was added triphenylphosphine (27 g, 103 mmol) and the mixture was heated under reflux for 18 hours. The solvent was evaporated under reduced pressure and hexane was added. The mixture was passed through a plug of silica gel, washing well with hexane. The solvent was evaporated under reduced pressure to give the title compound (12 g). $^1$H NMR (250 MHz, CDCl$_3$) δ 7.91 (1H, d, J 2.5 Hz), 7.82–7.67 (5H, m), 7.56 (1H, dd, J 8.80, 2.5 Hz), 7.33 (1H, d, J 8.8 Hz), and 5.53 (2H, s).

DESCRIPTION 11

1-(4-Benzyloxy-3-bromophenyl)-5-trifluoromethyl-(1H)-tetrazole

To a suspension of sodium azide (3 g) in dimethylformamide (50 ml) was slowly added a solution of 5-(1-chloro-2,2,2-trifluoroacetimidato)-2-benzyloxy-1-bromobenzene (Description 10; 12 g, 31.8 mmol) in dimethylformamide (25 ml) over 30 minutes. The mixture was stirred at room temperature for 2 hours, then water and ethyl acetate were added. The organic phase was washed with water (5 times) and saturated brine, dried (MgSO$_4$) and the solvent was evaporated under reduced pressure. The residue was purified by chromatography on silica gel, eluting with hexane/ethyl acetate, to give the title compound (11.6 g) mp 66–68° C. $^1$H NMR (250 MHz, CDCl$_3$) δ 7.74 (1H, d, J 2.6 Hz), 7.5–7.3 (6H, m), 7.12 (1H, d, J 8.9 Hz), and 5.27 (2H, s).

DESCRIPTION 12

(5R,6S)-3-(2-Benzyloxy-5-(5-(trifluoromethyl)tetrazol-1-yl)phenyl)-6-phenyl-1-oxa-7-(tert-butoxycarbonyl)aza-spiro[4.5]dec-3-ene A mixture of (5R,6S)-3-tributylstannyl-6-phenyl-1-oxa-7-(tert-butoxycarbonyl)aza-spiro[4.5]dec-3-ene (Description 3; 2.0 g, 3.3 mmol), lithium chloride (1.29 g, 30.3 mmol) and 1-(4-benzyloxy-3-bromophenyl)-5-trifluoromethyl-(1H)-tetrazole (Description 11; 1.6 g, 4.0 mmol) in toluene (25 ml) was degassed before addition of tetrakis(triphenylphosphine) palladium (0) (0.192 g). The solution was degassed thoroughly and then was heated to 110° C. for 24 hours. Silica gel was added and the solvent was evaporated under reduced pressure. The residue was purified by column chromatography on silica gel, eluting with hexane/ethyl acetate (100:0 increasing to 85:15) to give the title compound (1.34 g). $^1$H NMR (360 MHz, CDCl$_3$) δ 7.47–7.88 (7H, m), 7.33 (1H, dd, J 8.8 2.7 Hz), 7.26–7.13 (5H, m), 6.7 (1H, t, J<2 Hz), 5.24 (1H, d, J 11.4 Hz), 5.18 (1H, d, J 11.4 Hz), 5.08 (1H, s), 4.90 (1H, dd, J 12.0, 1.9 Hz), 4.08 (1H, dd, J 12.1, 2.09 Hz), 4.08 (1H, dt, J 12.7 Hz), 3.11 (1H, m), 2.06 (1H, m), 1.76 (3H, m), and 1.32 (9H, s). m/z (ES$^+$) 634 (M+1)$^+$.

DESCRIPTION 13

2-Benzyloxy-5-nitroiodobenzene

Chloramine-T trihydrate (36 g, 127 mmol) was added to a mixture of 4-nitrophenol (15 g, 107 mmol) and sodium iodide (19.1 g, 127 mmol) in DMF (300 ml) at room temperature. The resulting dark red mixture was stirred at room temperature for 3 hours, poured into water (1.2 litres), acidified to pH 1 with aqueous hydrochloric acid (1M) and extracted with ethyl acetate. The organic extract was washed with sodium thiosulphate solution (10%) and brine, dried (MgSO$_4$) and the solvent was evaporated under reduced pressure. The residue was purified by flash column chromatography on silica gel eluting with hexane/ethyl acetate (50:50). The residue was dissolved in DMF (75 ml) and benzyl bromide (10.7 ml, 90 mmol) and potassium carbonate (66 g, 480 mmol) were added. The mixture was stirred at room temperature over night, poured into water (1 litre) and extracted with ethyl acetate. The organic extract was washed with brine, dried (MgSO$_4$), and the solvent was evaporated under reduced pressure. The residue was purified by flash column chromatography on silica gel eluting with hexane/dichloromethane/ethyl acetate (50:50:1) to give the title compound as a colorless solid (24.3 g, 64%). $^1$H NMR (360 MHz, CDCl$_3$) δ 8.70 (1H, d, J 2.7 Hz), 8.21 (1H, dd, J 9.13, 2.7 Hz), 7.48–7.34 (5H, m), 6.89 (1H, d, J 9.14 Hz), and 5.27 (2H, s).

DESCRIPTION 14

4-Benzyloxy-3-iodoaniline

Iron powder (12.5 g, 224 mmol) was added to a suspension of 2-benzyloxy-5-nitroiodobenzene (Description 13; 10 g, 28 mmol) in water (300 ml) and acetic acid (75 ml) and the mixture was stirred at 80° C. for 12 hours. The mixture was allowed to cool to room temperature and filtered through Hyflo™, washing with 4:1 water:acetic acid and ethyl acetate. The filtrate was extracted with ethyl acetate, and the organic extract was evaporated under reduced pressure. Saturated aqueous sodium hydrogen carbonate was added and the mixture was extracted with ethyl acetate. The organic extract was washed with brine, dried (MgSO$_4$), and the solvent was evaporated under reduced pressure to give the title compound as a brown oil (9 g, 99% yield). $^1$H NMR (360 MHz, CDCl$_3$) δ 7.49–7.47 (2H, m), 7.40–7.28 (3H, m), 7.19 (1H, d, J 2.4 Hz), 6.70 (1H, d, J 8.6 Hz), 6.62 (1H, dd, J 2.4, 8.6 Hz), and 5.04 (2H, s). m/z (ES$^+$) 326 (M+1)$^+$.

DESCRIPTION 15

N-(4-Benzyloxy-3-iodophenyl)trifluoroacetamide

Prepared from the compound of Description 14 according to the method of Description 9. $^1$H NMR (360 MHz, CDCl$_3$) δ 7.96 (1H, d, J 2.6 Hz), 7.73 (1H, br s), 7.54 (1H, dd, J 8.8, 2.6 Hz), 7.48–7.31 (5H, m), 6.85 (1H, d, J 8.8 Hz), and 5.16 (2H, s).

DESCRIPTION 16

1-(4-Benzyloxy-3-iodophenyl)-2-trifluoromethyl-1H-imidazole

Triphenylphosphine (3.11 g, 11.88 mmol) was added to a suspension of N-(4-benzyloxy-3-iodophenyl)trifluoroacetamide (Description 15; 2.5 g, 5.94 mmol) in carbon tetrachloride (35 ml) and the mixture was heated under reflux for 24 hours. The mixture was then allowed to cool and the solvent was evaporated under reduced pressure. Hexane was then added and the mixture was heated under reflux for 1 hour. The mixture was filtered and the solvent was evaporated under reduced pressure. The residue was dissolved in THF (20 ml), aminoacetaldehyde dimethyl acetal (2.5 ml, 22.9 mmol) was added and the mixture was stirred at room temperature overnight. The solvent was evaporated under reduced pressure and acetic acid was added. The mixture was heated under reflux for 3 hours, cooled and diluted with water. The mixture was basified and extracted with ethyl acetate. The organic extract was dried (MgSO$_4$) and the solvent was evaporated under reduced pressure. The residue was purified by flash column chromatography on silica gel eluting with hexane/ethyl acetate (75:25) to give the title compound as a pale yellow oil (900 mg, 34%). $^1$H NMR (360 MHz, CDCl$_3$) δ 7.80 (1H, d, J 2.5 Hz), 7.50 (2H, m), 7.44–7.43 (3H, m), 7.30 (1H, dd, J 2.5, 8.7 Hz), 7.20 (1H, s), 7.10 (1H, s), 6.91 (1H, d, J 8.7 Hz), and 5.22 (2H, s). m/z (ES$^+$) 445 (M+1).

EXAMPLE 1

(3R,5R,6S)-3-(2-Hydroxy-5-(5-(trifluoromethyl)tetrazol-1-yl)phenyl)-6-phenyl-1-oxa-7-(tert-butoxycarbonyl)aza-spiro[4.5]decane A solution of (5R,6S)-3-(2-benzyloxy-5-(5-(trifluoromethyl)tetrazol-1-yl)phenyl-6-phenyl-1-oxa-7-(tert-butoxycarbonyl)aza-spiro[4.5]dec-3-ene (Description 12; 0.4 g, 0.63 mmol) in ethyl acetate (25 ml) and methanol (25 ml) was hydrogenated in the presence of palladium hydroxide (0.170 g) for 16 hours at 45 psi. The solution was filtered and the solvent was evaporated under reduced pressure. The residue was purified by column chromatography on silica gel eluting with hexane/ethyl acetate (7:1 increasing to 3:1) to give (3S,5R,6S)-3-(2-hydroxy-5-(5-(trifluoromethyl)tetrazol-2-yl)phenyl)-6-phenyl-1-oxa-7-(tert-butoxycarbonyl)aza-spiro[4.5]decane (288 mg), $^1$H NMR (360 MHz, CDCl$_3$) δ 7.60 (1H, br s), 7.53 (1H, d, J 7.55 Hz), 7.31–7.15 (5H, m), 6.9 (1H, d, J 8.49 Hz), 5.3 (1H, s), 4.26 (1H, dd, J 9.33, 6.91 Hz), 3.98 (2H, m), 3.68 (1H, m), 2.86 (1H, m), 2.55 (1H, dd, J 13.2, 9.3 Hz), 2.22 (2H, m), 1.75 (3H, m), and 1.32 (9H, s); and the title compound (3R,5R,6S)-3-(2-hydroxy-5-(5-(trifluoromethyl)tetrazol-1-yl)phenyl)-6-phenyl-1-oxa-7-(tert-butoxycarbonyl)aza-spiro[4.5]decane (25 mg), $^1$H NMR (360 MHz, CDCl$_3$) δ 7.59 (2H, d, J 7.5 Hz), 7.32 (2H, t, J 7.4 Hz), 7.26–7.23 (2H, m), 7.17 (1H, dd, J 8.59, 2.49 Hz), 7.03 (1H, d, J 8.63 Hz), 5.45 (1H, s), 4.34 (1H, dd, J 8.95 Hz), 7.13 Hz), 3.97 (3H, m), 2.74 (2H, m), 2.32 (1H, td, J 13.0, 8.3 Hz), 1.86 (2H, m), and 1.52 (9H, s).

EXAMPLE 2

(3R,5R,6S)-3-(2-Methoxy-5-(5-(trifluoromethyl)tetrazol-1-yl)phenyl)-6-phenyl-1-oxa-7-(tert-butoxycarbonyl)aza-spiro[4.5]decane To a solution of (3R,5R,6S)-3-(2-hydroxy-5-(5-(trifluoromethyl)tetrazol-1-yl)phenyl)-6-phenyl-1-oxa-7-

(tert-butoxycarbonyl)aza-spiro[4.5]decane (Example 1; 25 mg) in dimethylformamide (1 ml) and potassium carbonate (0.3 g) was added methyl iodide (0.02 ml). The solution was stirred at room temperature for 20 minutes, then water (50 ml) and ethyl acetate (50 ml) were added. The organic phase was dried (MgSO$_4$) and the solvent was evaporated under reduced pressure to give the title compound. m/z (ES$^+$) 504 (MH$^+$—C$_4$H$_8$).

EXAMPLE 3

(3R,5R,6S)-3-(2-Methoxy-5-(5-(trifluoromethyl) tetrazol-1-yl)phenyl)-6-phenyl-1-oxa-7-aza-spiro [4.5]decane Hydrochloride (3R,5R,6S)-3-(2-Methoxy-5-(5-(trifluoromethyl)tetrazol-1-yl)phenyl)-6-phenyl-1-oxa-7-(tert-butoxycarbonyl)aza-spiro[4.5]decane (Example 2) was dissolved in trifluoroacetic acid (5 ml) and the mixture was stirred at room temperature for 20 minutes. The solvent was evaporated under reduced pressure and the residue was partitioned between ethyl acetate and aqueous potassium carbonate solution. The organic phase was dried (MgSO$_4$) and the solvent was evaporated under reduced pressure. The residue was purified by column chromatography on silica gel, eluting with dichloromethane/methanol/aqueous ammonio (100:0:0 increasing to 95:5:0.2) to give (3R,5R,6S)-3-(2-methoxy-5-(5-(trifluoromethyl)tetrazol-1-yl)phenyl)-6-phenyl-1-oxa-7-aza-spiro[4.5]decane. $^1$H NMR (360 MHz, CDCl$_3$) δ 7.50 (2H, m), 7.34 (3H, m), 7.22 (1H, dd, J 8.79 Hz and 2.6 Hz), 7.07 (1H, d, J 2.6 Hz), 6.85 (1H, d, J 8.79 Hz), 3.99 (1H, t, J 7.7 Hz), 3.75 (3H, s), 3.65 (2H, m), 3.27 (1H, bd), 2.79 (1H, td J 12.5 Hz and 2.5 Hz), 2.34 (1H, m), 2.23–2.09 (2H, m), 1.93 (1H, d J 15.3 Hz), 1.70–1.57 (3H, m). m/z (ES$^+$) 460 (M+1).

The residue was dissolved in dichloromethane and ethereal hydrogen chloride (1M) was added. The solvent was evaporated under reduced pressure and the residue was triturated with diethyl ether. The solid was collected and dried in vacuo to give the title compound. m/z (ES$^+$) 460 (M+1).

EXAMPLE 4

(3R,5R,6S)-3-[2-Benzyloxy-5-(2-trifluoromethyl-1H-imidazol-1-yl)phenyl]-6-phenyl-1-oxa-7-(tert-butoxycarbonyl)aza-spiro[4.5]decane A mixture of (5R,6S)-6-phenyl-1-oxa-7-(tert-butoxycarbonyl)aza-spiro[4.5]dec-3-ene (Description 5; 350 mg, 1.11 mmol), 1-(4-benzyloxy-3-iodophenyl)-2-trifluoromethyl-1H-imidazole (Description 16; 800 mg, 1.8 mmol), tetrabutylammonium chloride (308 mg, 1.11 mmol), lithium chloride (472 mg, 11.1 mmol), and potassium formate (186 mg, 2.22 mmol) in DMF (20 ml) was degassed using a firestone valve. Palladium acetate (25 mg, 0.111 mmol) was added and the mixture was degassed, then stirred at 60° C. for 96 hours, adding further portions of potassium formate (93 mg, 1.11 mmol) and palladium acetate (12.5 mg, 0.056 mmol) at 24 hour intervals. The mixture was cooled, filtered and extracted with ethyl acetate. The organic extract was washed with water, dried (MgSO$_4$) and the solvent was evaporated under reduced pressure. The residue was purified by flash column chromatography on silica gel, eluting with hexane/ethyl acetate (75:25), to give the title compound as a colorless foam (300 mg, 43%). $^1$H NMR (360 MHz, CDCl$_3$) δ 7.56 (2H, m), 7.41 (4H, m), 7.32–7.20 (5H, m), 7.12 (2H, m), 6.99–6.91 (2H, m), 5.31 (1H, br s), 5.15 (2H, s), 4.30 (1H, t, J 7.4 Hz), 4.00–3.85 (2H, m), 2.77 (1H, td), 2.59 (1H, m), 2.16 (2H, m), 1.97 (1H, m), 1.64 (3H, m), and 1.42 (9H, s). m/z (ES$^+$) 634 (M+1).

EXAMPLE 5

(3R,5R,6S)-3-[2-Hydroxy-5-(2-trifluoromethyl-1H-imidazol-1-yl)phenyl]-6-phenyl-1-oxa-7-(tert-butoxycarbonyl)aza-spiro[4,5]decane Palladium hydroxide (200 mg) was added to a solution of (3R,5R,6S)-3-[2-benzyloxy-5-(2-trifluoromethyl-1H-imidazol-1-yl)phenyl]-6-phenyl-1-oxa-7-(tert-butoxycarbonyl)aza-spiro[4,5]decane (Example 4; 290 mg, 0.46 mmol) in methanol (10 ml) and ethyl acetate (3 ml) and the mixture was shaken under hydrogen (50 psi) for 72 hours. The mixture was filtered, washing with ethyl acetate, and the solvent was evaporated under reduced pressure. The residue was purified by flash column chromatography on silica gel, eluting with hexane/ethyl acetate (70:30), to give the title compound as a colorless solid (140 mg, 56%). $^1$H NMR (360 MHz, CDCl$_3$) δ 7.59 (2H, m), 7.35–7.26 (3H, m), 7.20 (1H, m), 7.10 (3H, m(, 6.92 (1H, m), 5.44 (1H, br s), 4.30 (1H, m), 4.04–3.94 (2H, m), 3.82 (1H, m), 2.80–2.72 (2H, m), 2.33 (1H, m), 1.84 (2H, m), 1,72 (1H, m), and 1.63 (9H, s). m/z (ES$^+$) 544 (M+1).

EXAMPLE 6

(3R,5R,6S)-3-[2-(Difluoromethoxy)-5-(2-trifluoromethyl-1H-imidazol-1-yl)phenyl]-6-phenyl-1-oxa-7-(tert-butoxycarbonyl)aza-spiro[4,5]decane Ethyl chlorodifluoroacetate (1 ml, 7.9 mmol) was added to a mixture of (3R,5R,6S)-3-[2-hydroxy-5-(2-trifluoromethyl-1H-imidazol-1-yl)phenyl]-6-phenyl-1-oxa-7-(tert-butoxycarbonyl)aza-spiro[4,5]decane (Example 5; 130 mg, 0.24 mmol) and potassium carbonate in DMF (5 ml) and the mixture was stirred at 80° C. for 24 hours. The mixture was allowed to cool, poured into water and extracted with ethyl acetate. The organic extract was washed with water, dried (MgSO$_4$) and the solvent was evaporated under reduced pressure. The residue was purified by flash column chromatography on silica gel eluting with hexane/ethyl acetate (70:30) to give the title compound as a colorless foam (70 mg, 50%). $^1$H NMR (360 MHz, CDCl$_3$) δ 7.59 (2H, m), 7.40 (1H, s), 7.33 (2H, m), 7.26 (4H, m), 7.15 (1H, m), 6.62 (1H, t, J 72.7 Hz), 5.36 (1H, s), 4.33 (1H, m), 3.98–3.84 (3H, m), 2.75–2.68 (2H, m), 2.24 (1H, m), 1.81 (1H, m), 1.70 (3H, m), and 1.47 (9H, s). m/z (ES$^+$) 594 (M+1).

EXAMPLE 7

(3R,5R,6S)-3-[2-(Difluoromethoxy)-5-(2-trifluoromethyl-1H-imidazol-1-yl)phenyl]-6-phenyl-1-oxa-7-aza-spiro[4,5]decane Hydrochloride Ethanolic hydrogen chloride (5M, 3 ml) was added to a solution of (3R,5R,6S)-3-[2-(difluoromethoxy)-5-(2-trifluoromethyl-1H-imidazol-1-yl)phenyl]-6-phenyl-1-oxa-7-(tert-butoxycarbonyl)aza-spiro[4,5]decane (Example 6; 60 mg, 0.1 mmol) in ethanol (1 ml) and the mixture was stirred at room temperature overnight. The solvent was evaporated under reduced pressure, saturated aqueous sodium hydrogen carbonate was added and the mixture was extracted with ethyl acetate. The organic extract was dried (MgSO$_4$) and the solvent was evaporated under reduced pressure. The residue was purified by flash column chromatography on silica gel eluting with dichloromethane/methanol/aqueous ammonia (88:12:1.2). The residue was dissolved in ethyl acetate (2 ml) and ethereal hydrogen chloride (1M) was added. The solvent was evaporated under reduced pressure and the residue was recrystallised from ethyl acetate to give the title compound as a colorless solid (30 mg, 57%). $^1$H NMR (360 MHz, $D_2O$) δ 7.56–7.23 (10H, m), 6.63 (1H, t, J 72.9 Hz), 4.32 (1H, m), 4.10 (1H, t), 3.73 (1H, m), 3.50 (1H, dt), 3.21 (1H, td), 2.42–2.25 (2H, m), 2.42–2.25 (1H, m), 2.20–2.14 (1H, m), 2.02–1.92 (3Hm), and 1.84 (1H, m). m/z ($ES^+$) 494 (M+1).

What is claimed is:

1. A compound of the formula (I):

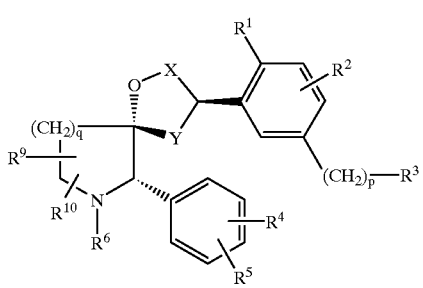

(I)

wherein

X represents $-CH_2-$, $-CH_2CH_2-$ or $-CH_2CH_2CH_2-$;

Y represents $-CH_2-$ or $-CH_2CH_2-$, with the proviso that the sum total of carbon atoms in X and Y is 2 or 3;

$R^1$ represents halogen, hydroxy, $C_{1-6}$alkyl, $C_{1-6}$alkoxy, $C_{1-6}$alkylthio, $C_{1-6}$alkoxy$C_{1-4}$alkyl, fluoro$C_{1-6}$alkyl, fluoro$C_{1-6}$alkoxy, fluoro$C_{1-6}$alkylthio, fluoro$C_{1-6}$alkoxy$C_{1-4}$alkyl, $C_{3-7}$cycloalkyl, $C_{3-7}$cycloalkyl$C_{1-4}$alkyl, $C_{2-6}$alkenyloxy, cyano, phenoxy, benzyloxy, $NR^aR^b$, $SR^a$, $SOR^a$, $SO_2R^a$, or $OSO_2R^a$, where $R^a$ and $R^b$ each independently represent hydrogen, $C_{1-4}$alkyl or fluoro$C_{1-4}$alkyl;

$R^2$ represents hydrogen, halogen, $C_{1-6}$alkyl or $C_{1-6}$alkoxy;

or when $R^2$ is adjacent to $R^1$, they may be joined together such that there is formed a 5- or 6-membered saturated or unsaturated ring containing one or two oxygen atoms;

$R^3$ represents a 5- or 6-membered aromatic heterocyclic group containing 1, 2, 3 or 4 heteroatoms, selected from nitrogen, oxygen and sulphur, which group is optionally substituted by one or two groups selected from $C_{1-6}$alkyl, $C_{1-6}$alkoxy, $C_{3-7}$cycloalkyl, $C_{3-7}$cycloalkyl$C_{1-4}$alkyl, trifluoromethyl, $OCF_3$, $NO_2$, CN, $SR^a$, $SOR^a$, $SO_2R^a$, $COR^a$, $CO_2R^a$, phenyl, $-(CH_2)_rNR^aR^b$, $-(CH_2)_rNR^aCOR^b$, $-(CH_2)_rCONR^aR^b$, or $CH_2C(O)R^a$, where $R^a$ and $R^b$ are each independently hydrogen or $C_{1-4}$alkyl and r is zero, 1 or 2;

$R^4$ represents hydrogen, halogen, $C_{1-6}$alkyl, $C_{1-6}$alkoxy, $CF_3$, $OCF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ are as previously defined;

$R^5$ represents hydrogen, halogen, $C_{1-6}$alkyl, $C_{1-6}$alkoxy substituted by $C_{1-4}$alkoxy or $CF_3$;

$R^6$ represents hydrogen, $COR^a$, $CO_2R^a$, $COCONR^aR^b$, $COCO_2R^a$, $C_{1-6}$alkyl optionally substituted by a group selected from ($CO_2R^a$, $CONR^aR^b$, hydroxy, CN, $COR^a$, $NR^aR^b$, $C(NOH)NR^aR^b$, $CONHphenyl(C_{1-4}alkyl)$, $COCO_2R^a$, $CONHNR^aR^b$, $C(S)NR^aR^b$, $CONR^aC_{1-6}alkylR^{12}$, $CONR^{13}C_{2-6}alkenyl$, $CONR^{13}C_{2-6}alkynyl$, $COCONR^aR^b$, $CONR^aC(NR^b)NR^a$, $R^b$, $CONR^aheteroaryl$, and phenyl optionally substituted by one, two or three substituents selected from $C_{1-6}alkyl$, $C_{1-6}alkoxy$, halogen and trifluoromethyl);

or $R^6$ represents a group of the formula $-CH_2C\equiv CCH_2NR^7R^8$ where $R^7$ and $R^8$ are as defined below;

or $R^6$ represents $C_{1-6}$alkyl, optionally substituted by oxo, substituted by a 5-membered or 6-membered heterocyclic ring containing 1, 2 or 3 nitrogen atoms optionally substituted by =O or =S and optionally substituted by a group of the formula $ZNR^7R^8$ where Z is $C_{1-6}$alkylene or $C_{3-6}$cycloalkyl;

$R^7$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy or hydroxyl;

$R^8$ is hydrogen or $C_{1-4}$alkyl, $C_{3-7}$cycloalkyl, $C_{3-7}$cycloalkyl$C_{1-4}$alkyl, or $C_{2-4}$alkyl substituted by $C_{1-4}$alkoxy, hydroxyl or a 4, 5 or 6 membered heteroaliphatic ring containing one or two heteroatoms selected from N, O and S;

or $R^7$, $R^8$ and the nitrogen atom to which they are attached form a heteroaliphatic ring of 4 to 7 ring atoms, optionally substituted by one or two groups selected from hydroxy or $C_{1-4}$alkoxy optionally substituted by a $C_{1-4}$alkoxy or hydroxyl group, and optionally containing a double bond, which ring may optionally contain an oxygen or sulphur ring atom, a group $S(O)$ or $S(O)_2$ or a second nitrogen atom which will be part of a NH or $NR^c$ moiety where $R^c$ is $C_{1-4}$alkyl optionally substituted by hydroxy or $C_{1-4}$alkoxy;

or $R^7$, $R^8$ and the nitrogen atom to which they are attached form a non-aromatic azabicyclic ring system of 6 to 12 ring atoms;

or Z, $R^7$ and the nitrogen atom to which they are attached form a heteroaliphatic ring to 4 to 7 ring atoms which may optionally contain an oxygen ring atom;

$R^9$ and $R^{10}$ each independently represent hydrogen, halogen, $C_{1-6}$alkyl, $CH_2OR^d$, oxo, $CO_2R^a$ or $CONR^aR^b$ where $R^a$ and $R^b$ are as previously defined and $R^d$ represents hydrogen, $C_{1-6}$alkyl or phenyl;

$R^{12}$ represents $OR^a$, $CONR^aR^b$ or heteroaryl;

$R^{13}$ represents H or $C_{1-6}$alkyl;

p is zero or 1; and q is 2;

or pharmaceutically acceptable salt thereof.

2. A compound of the formula (Ia):

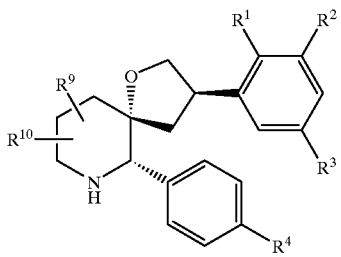

(Ia)

wherein $R^1$, $R^2$, $R^3$, $R^4$, $R^9$ and $R^{10}$ are as defined in claim 1; or a pharmaceutically acceptable salt thereof.

3. A compound as claimed in claim 1 wherein $R^1$ is a $C_{1-4}$alkoxy, fluoro$C_{1-4}$alkoxy or $C_{3-5}$cycloalkoxy group.

4. A compound as claimed in claim 1 wherein $R^2$ is a hydrogen, fluorine or chlorine atom.

5. A compound as claimed in claim 1 wherein $R^3$ is a group selected from pyrrole, furan, thiene, pyridine, pyrazole, imidazole, oxazole, isoxazole, thiazole, isothiazole, pyrazine, pyrimidine, pyridazone, triazole, oxadiazole, thiadiazole, triazine, and tetrazole, each heteroaryl group being optionally substituted as defined in claim 1.

6. A compound as claimed in claim 5 wherein $R^3$ is the group

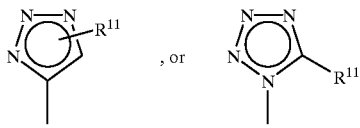

, or where $R^{11}$ is hydrogen, halogen, $C_{1-6}$alkyl, $C_{1-6}$alkoxy, $CF_3$, $OCF_3$, $NO_2$, $CN$, $SR^a$, $SOR^a$, $SO_2R^a$, $COR^a$, $CO_2R^a$, $(CH_2)_r CONR^aR^b$, $(CH_2)_r NR^aR^b$ or $(CH_2)_r NR^a COR^b$, where $R^a$ and $R^b$ are hydrogen or $C_{1-4}$alkyl, and r is zero, 1 or 2.

7. A compound as claimed in claim 1 wherein $R^4$ is a hydrogen atom or a fluorine atom.

8. A compound as claimed in claim 1 wherein $R^5$ is a hydrogen atom.

9. A compound as claimed in claim 1 wherein $R^6$ is a hydrogen atom.

10. A compound as claimed in claim 1 wherein $R^9$ and $R^{10}$ are both hydrogen atoms.

11. A compound selected from:
(3R,5R,6S)-3-(2-methoxy-5-(5-(trifluoromethyl)tetrazol-1-yl)phenyl)-6-phenyl-1-oxa-7-aza-spiro[4.5]decane;
(3R,5R,6S)-3-[2-(difluoromethoxy)-5-(2-trifluoromethyl-1H-imidazol-1-yl)phenyl]-6-phenyl-1-oxa-7-aza-spiro[4.5]decane;
or a pharmaceutically acceptable salt thereof.

12. A pharmaceutical composition comprising a compound as claimed in claim 1, together with at least one pharmaceutically acceptable carrier or excipient.

13. A method for the treatment of physiological disorders associated with an excess of tachykinins, which method comprises administration to a patient in need thereof of a tachykinin reducing amount of a compound according to claim 1.

14. A method according to claim 13 for the treatment of pain or inflammation, migraine, emesis or postherpetic neuralgia.

15. A process for the preparation of a compound as claimed in claim 1 which comprises:

(A.1), where X is —$CH_2$— and Y is —$CH_2$— or —$CH_2CH_2$—, reduction of a compound of formula (IIA)

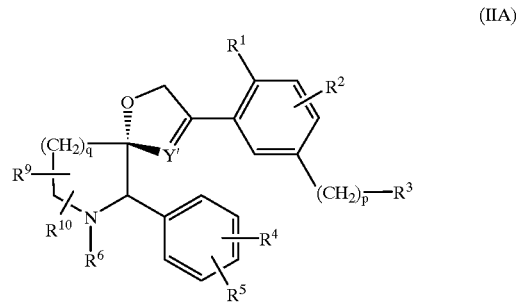

(IIA)

wherein $R^1$, $R^2$, $R^3$, $R^4$, $R^5$, $R^6$, $R^9$, $R^{10}$, p and q are as defined in claim 1 and Y' is —CH= or —$CH_2$CH=; or (A.2), reduction of a compound of formula (IIB)

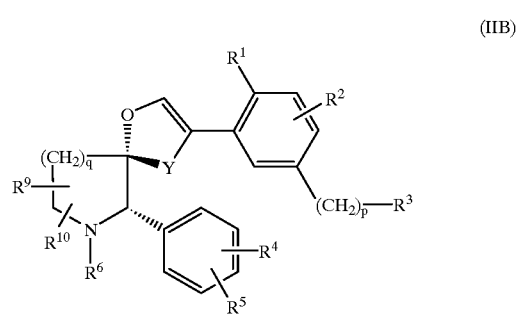

(IIB)

or (B), interconversion of a corresponding compound of formula (I) in which $R^6$ is H, i.e. a compound of formula (III)

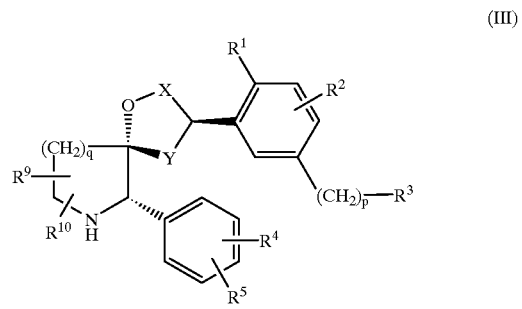

(III)

wherein X, Y, $R^1$, $R^2$, $R^3$, $R^4$, $R^5$, $R^9$, $R^{10}$, p and q are as defined in claim 1 by reaction with a compound of formula (IV):

LG-$R^{6a}$ (IV)

where $R^{6a}$ is a group of the formula $R^6$ as defined in claim 1 (other than H) or a precursor therefor and LG is a leaving group; and, if $R^{6a}$ is a precursor group, converting it to a group $R^6$; or (C), where p is zero and $R^3$ is a tetrazol-1-yl group, reaction of an intermediate of formula (V)

(V)

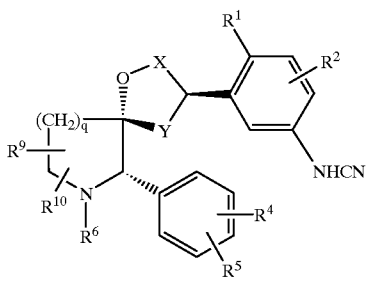

with ammonium chloride and sodium azide; or (D), a coupling reaction between a compound of formula (VIA) and (VIB)

(VIA)

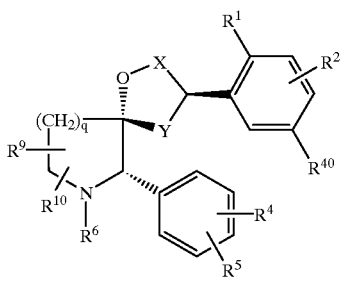

(VIB)

$R^3\text{—}(CH_2)_p\text{—}R^{41}$ wherein one of $R^{40}$ and $R^{41}$ is $B(OH)_2$ or $Sn(alkyl)_3$ or a derivative thereof, and the other is a leaving group; or (E), where X is —CH$_2$—, cyclisation of a compound of formula (VII)

(VII)

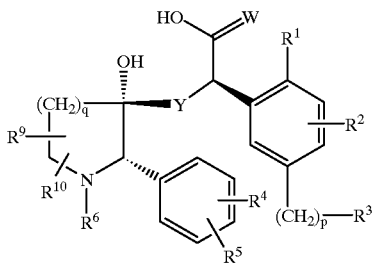

wherein W is an oxygen atom or two hydrogen atoms, in the presence of a dehydrating reagent; or (F), where $R^1$ is a cyclopropyloxy group, reaction of a compound of formula (VIII)

(VIII)

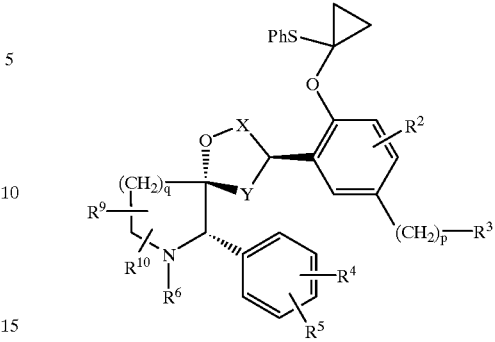

with lithium naphthalenide in tetrahydrofuran; or (G), reaction of a compound of formula (IX)

(IX)

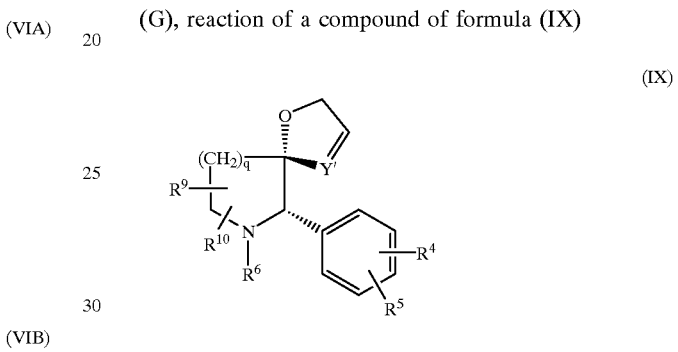

wherein Y' is —CH= or —CH$_2$CH=, with a compound of formula (X), (X)

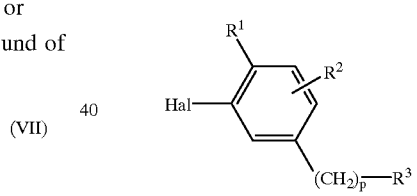

where Hal is chlorine, bromine or iodine, by a reductive Heck reaction;

each process being followed, where necessary, by the removal of any protecting group where present;

and when the compound of formula (I) is obtained as a mixture of enantiomers or diastereoisomers, optionally resolving the mixture to obtain the desired enantiomer;

and/or, if desired, converting the resulting compound of formula (I) or a salt thereof, into a pharmaceutically acceptable salt thereof.

\* \* \* \* \*